(12) United States Patent
Lv et al.

(10) Patent No.: US 11,001,837 B2
(45) Date of Patent: May 11, 2021

(54) LOW-FREQUENCY MUTATIONS ENRICHMENT SEQUENCING METHOD FOR FREE TARGET DNA IN PLASMA

(71) Applicant: Geneplus—Beijing, Beijing (CN)

(72) Inventors: Xiaoxing Lv, Beijing (CN); Xin Yi, Beijing (CN); Meiru Zhao, Beijing (CN); Yanfang Guan, Beijing (CN); Tao Liu, Beijing (CN); Ling Yang, Beijing (CN)

(73) Assignee: Geneplus—Beijing, Beijing (CN)

( * ) Notice: Subject to any disclaimer, the term of this patent is extended or adjusted under 35 U.S.C. 154(b) by 322 days.

(21) Appl. No.: 15/751,722

(22) PCT Filed: Feb. 18, 2016

(86) PCT No.: PCT/CN2016/074058
§ 371 (c)(1),
(2) Date: Feb. 9, 2018

(87) PCT Pub. No.: WO2017/024784
PCT Pub. Date: Feb. 16, 2017

(65) Prior Publication Data
US 2018/0371453 A1 Dec. 27, 2018

(30) Foreign Application Priority Data

Aug. 10, 2015 (CN) .......................... 201510487759.1

(51) Int. Cl.
| | | |
|---|---|---|
| *C12P 19/34* | (2006.01) | |
| *C12N 15/10* | (2006.01) | |
| *G16B 30/00* | (2019.01) | |
| *G16B 40/00* | (2019.01) | |
| *G16B 40/30* | (2019.01) | |
| *G16B 20/20* | (2019.01) | |
| *C12Q 1/6806* | (2018.01) | |
| *A61P 35/00* | (2006.01) | |
| *C12Q 1/6853* | (2018.01) | |
| *C12Q 1/6869* | (2018.01) | |
| *C12Q 1/6886* | (2018.01) | |
| *C40B 50/10* | (2006.01) | |
| *G16B 30/10* | (2019.01) | |
| *G16H 20/10* | (2018.01) | |
| *C40B 40/08* | (2006.01) | |

(52) U.S. Cl.
CPC .......... *C12N 15/1072* (2013.01); *A61P 35/00* (2018.01); *C12N 15/1058* (2013.01); *C12N 15/1065* (2013.01); *C12Q 1/6806* (2013.01); *C12Q 1/6853* (2013.01); *C12Q 1/6869* (2013.01); *C12Q 1/6886* (2013.01); *C40B 50/10* (2013.01); *G16B 20/20* (2019.02); *G16B 30/00* (2019.02); *G16B 40/00* (2019.02); *G16B 40/30* (2019.02); *C12N 15/1003* (2013.01); *C12N 15/1093* (2013.01); *C40B 40/08* (2013.01); *G16B 30/10* (2019.02); *G16H 20/10* (2018.01)

(58) Field of Classification Search
CPC .................................................... C12Q 1/6869
See application file for complete search history.

(56) References Cited

U.S. PATENT DOCUMENTS

| | | | | |
|---|---|---|---|---|
| 2012/0289412 A1* | 11/2012 | Seitz | ................... | C12Q 1/6855 506/2 |
| 2013/0012399 A1* | 1/2013 | Myers | ................. | C12Q 1/6806 506/2 |

FOREIGN PATENT DOCUMENTS

| | | |
|---|---|---|
| CN | 104153003 A | 11/2014 |
| CN | 105063208 A | 11/2015 |

OTHER PUBLICATIONS

Castellanos-Rizaldos et al., Clin. Chem. 58(7), 1130-11-38 (2012). (Year: 2012).*
Jin Li, et al., "Two-round coamplification at lower denaturation temperature-PCR (COLDPCR)-based sanger sequencing identifies a novel spectrum of low-level mutations in lung adenocarcinoma", Human Mutation, Nov. 2009, vol. 30, Issue 11, abstract.
International Search Report dated May 16, 2016 in connection with PCT International Application PCT/CN2016/074058.
Xu Lin-Lin, et al., "The principle and application of COLD-PCR", Journal of Biology, Dec. 2012, vol. 29, No. 6 including English language.
Jin Li, et al., "Two-round COLD-PCR-based Sanger sequencing identifies a novel spectrum of low-level mutations in lung adenocarcinoma", Author manuscript, published in final edited form in Hum Mutat., Nov. 2009, vol. 30, Issue 11.

* cited by examiner

*Primary Examiner* — Kenneth R Horlick
(74) *Attorney, Agent, or Firm* — John P. White

(57) ABSTRACT

The present invention provides a low-frequency mutation enrichment sequencing method for free target DNA in plasma, comprising plasma DNA extraction and library construction, general library TT COLD PCR amplification enrichment, probe enrichment capture, PCR and sequencing of captured products, and positive and negatice double-strand error-correction low-frequency information analysis.

9 Claims, 1 Drawing Sheet
Specification includes a Sequence Listing.

LOW-FREQUENCY MUTATIONS ENRICHMENT SEQUENCING METHOD FOR FREE TARGET DNA IN PLASMA

CROSS-REFERENCE TO RELATED APPLICATIONS

This application is a § 371 national stage of PCT International Application No. PCT/CN2016/074058, filed Feb. 18, 2016, claiming priority of Chinese Patent Application No. 201510487759.1, filed Aug. 10, 2015, the contents of each of which are hereby incorporated by reference into the application.

REFERENCE TO A SEQUENCE LISTING

This application incorporates by reference nucleotide and/or amino acid sequences which are present in the file named "180629_90354_Sequence_Listing_CAE.txt", which is 1.28 kilobytes in size, and which was created Jun. 29, 2018 in the IBM-PC machine format, having an operating system compatibility with MS-Windows, which is contained in the text file filed Jun. 29, 2018 as part of this application.

TECHNICAL FIELD

The present invention pertains to the technical field of high-throughput sequencing in bioinformatics, in particular to a method for enrichment and sequencing of low-frequency mutations of target DNA in plasma.

BACKGROUND ART

In recent years, genetic test and diagnosis of free Cell-free Circulating Tumor DNA (ctDNA) in the blood of cancer patients has become a research hotspot. Studies have shown that circulating tumor DNA in the blood may become a new marker for early diagnosis, prognosis and accurate medical treatment of tumors. The detection of tumor markers in the circulating free DNA in the blood is carried out in a manner different from that of the detection methods of traditional tissue tumor markers, with the advantages of non-invasiveness, monitoring at any time and early screening. In addition, the sampling of circulating free DNA avoids the difficulty that current molecular diagnosis requires collecting cancer tissue as a source of specimen, and thus circulating free DNA is a promising tumor marker. However, in addition to free tumor DNA, there is also free normal tissue DNA in circulating blood, and the total amount of circulating DNA varies depending on individual difference, the occurring, developing and treating periods for tumor, etc. Furthermore, the frequency of ctDAN is often much lower than the corresponding frequency of cancer tissue, in particular, the abundance of ctDNA in the plasma from patients with early-stage cancer is even at the level of 0.01%. Therefore, accurate detection of low frequency mutations is the urgent problem to be solved in the clinical application of plasma ctDNA.

In order to effectively realize accurate detection of low-frequency mutations in plasma ctDNA and to fully exploit application potential, it is necessary to powerfully combine the techniques for enrichment and amplification with highly sensitive detection techniques. However, currently the related technologies such as preMiDTM, CAPP-Seq and Duplex Sequencing can only achieve the detection of low-frequency mutations to a certain extent, and its related practical application is still limited more or less. preMiDTM integrates three technologies, i.e. mutation bias amplification ARMS, fluorescence quantitative PCR and high resolution melting curve analysis (HRM), to achieve detection of trace mutation in plasma of non-cell system, but its detection sensitivity can only reach about 1%, and only for gene analysis of some hotspot mutations. Technological principle of CAPP-Seq lies in the combination of high-throughput sequencing technology and the target area capturing technology for use in plasma ctDNA, where samples are targeted and captured, and then subjected to deep sequencing, and filtration treatment is carried out based on the relevant data; this technique can obtain not only more information about gene mutation, but also can obtain results of low-frequency mutations having a frequency of 0.2% or more at a high specificity of 98%, however, it is still far away from early screening based on plasma ctDNA. Duplex Sequencing performs forward and reverse double-stranded error correction based on a UID (unique identifier) label, which can correct almost all types of sequencing errors with detected mutation frequency of $10^{-7}$, but there is a huge limitation to this technique, namely, it requires a sequencing throughput higher than conventional sequencing. Furthermore, with respect to high-throughput sequencing for plasma ctDNA to achieve detection of about 0.01% of rare mutations, huge sample requirement is also a challenge.

SUMMARY OF THE INVENTION

The present invention provides a method for enrichment and sequencing of low-frequency mutations of target DNA in plasma to overcome the deficiencies existing in the prior art.

The method for enrichment and sequencing low-frequency mutation of target DNA in plasma provided by the present invention comprises the following steps:

(1) extraction of target DNA from plasma and library construction;

(2) amplification and enrichment by universal library TT-COLD PCR;

(3) enrichment and capture with probes, and amplification and sequencing of hybridization captured product;

(4) analysis on low-frequency information with forward and reverse double-strand error correction.

The flowchart of the method of the present invention is shown in FIG. 1.

Wherein the plasma in step (1) is from human peripheral blood, and the method for library construction is performed according to three-step enzymatic reaction, i.e. terminal repair, addition of "A" and library linker ligation.

The primers for the library linker are provided as follows:

```
The first strand of the linker:
TACACTCTTTCCCTACACGACGCTCTTCCGATCT,

The second strand of the linker:
GATCGGAAGAGCACACGTCTGAACTCCAGTCAC.
```

In the method of the present invention, the amplification and enrichment by universal library TT-COLD PCR in step (2) comprises the following steps:

1) determining the Tm value of the library; and 2) bypassing the specific Tc values present for each inserted fragment, enriching various types of mutations on all fragments in the library based on 1 pair of universal primers under one serial cycling condition; setting Tc min≈TM−2.5, followed by a gradual increase in Tc at a rate of 0.5° C., and performing full cold PCR under each Tc condition, respectively.

Further, the Tm value of the library in step 1) is determined by the following method: performing analysis on the library of the target DNA from plasma using a pair of primers by fluorescence quantitative PCR according to melting curve to obtain Tm value of the library; the sequence of the pair of primers is:

```
upstream primer:
AATGATACGGCGACCACCGAGATCTACACTCTTTCCCTACACGACGCTCT

TCCGATCT,
and downstream primer:
CAAGCAGAAGACGGCATACGAGATxxxxxxxxGTGACTGGAGTTCAGACG

TGTGCTCTTCCGATCT,
``` where xxxxxxxx is an index tag.

In the step (2) described above, the pair of universal primers are universal library TT-COLD PCR primers, the nucleotide sequences of which are:

```
upstream primer:
AATGATACGGCGACCACCGAGATCTACACTCTTTCCCTACACGACGCTCT

TCCGATCT, downstream primer:
CAAGCAGAAGACGGCATACGAGATxxxxxxxxGTGACTGGAGTTCAGACG

TGTGCTCTTCCGATCT,
``` where xxxxxxxx is an index tag.

In the step (2) described above, the one serial cycling condition is provided as follows:

| | | |
|---|---|---|
| 98° C. | 30 sec | — |
| 98° C. | 10 sec | 3 cycles |
| 55-65° C. | 15 sec | |
| 72° C. | 30 sec | |
| 98° C. | 10 sec | 4 cycles |
| 70° C. | 2 min | |
| Tc1 = TM−2° C. | 20 sec | |
| 55-65° C. | 15 sec | |
| 72° C. | 30 sec | |
| ... | Tc2; Tc3; Tc4 | 4 cycles/Tc |
| | (ΔT = 0.5° C.) | |
| 98° C. | 10 sec | 4 cycles |
| 70° C. | 2 min | |
| Tc5 = TM−0° C. | 20 sec | |
| 55-65° C. | 15 sec | |
| 72° C. | 30 sec | |
| 72° C. | 2 min | — |
| 4° C. | Storage | — |

In the step (3) of the present invention method, the enrichment and capture with probes is performing hybridization capture with an enrichment probe chip after the amplified library being qualified in quality control, and the hybridization capture products are subjected to PCR amplification and then sequencing;

the design method for the enrichment probe chip is set as follows: the capture range of the chip is determined based on the purpose of the target gene, at least one most important hotspot mutation site is determined within a certain base range with reference to the database to which the target DNA belongs; several primary types of mutations among multiple mutation types present with respect to this site are taken for reference, corresponding frequency of occurrence is used as the proportion occupied by the mutation in the total probe coverage level at the site; with respect to the hotspot mutation, a probe designed based on the human genome reference sequence hg19 is replaced with, a probe designed based on a mutant base, the probes for other sites are maintained unchanged, and the difference ratio between the total coverage of the probe for hotspot mutation and the coverage of normal probe for other regions is not less than 3:1, so as to achieve enrichment of hotspot mutation during capture.

In the method of the present invention, the specific procedures for the analysis on low-frequency information with forward and reverse double-strand error correction (RealSeq Pipeline) in step (4) are as follows:

1) based on the sequencing results, the first 12 bp bases of tested sequence 1 and the first 12 bp bases of tested sequence 2 of paired tested sequences are cut as tags, arranged according to alphabetical order, and connected having smaller tags in the front to form an index of 24 bp, at the same time, forward and reverse strands are selected according to the manner of arrangement and combination of tags;

2) external sorting is carried out on the index to achieve the purpose of gathering together all the tested sequences amplified from the same DNA template;

3) center clustering is carried out on the gathered tested sequences having the same index, each large cluster with the same index is gathered into several small clusters according to the Hamming distance between the sequences, with the Hamming distance between any two pairs of paired tested sequences in each small cluster not exceeding 10, so as to achieve the purpose of distinguishing tested sequences having the same index but coming from different DNA templates;

4) the repeated clusters of the same DNA template obtained in step 3) is screened; if the numbers of tested sequences of the forward strand and the reverse strand both reach two pairs or more, subsequent analysis is performed;

5) the clusters that satisfy the conditions in 4) were corrected to generate a pair of error-free new tested sequences; for each sequenced bases in the DNA template, if a certain base type of the sequenced base in the tested sequence of the forward strand reaches a consistence rate of 80%, and in the tested sequence of the reverse strand also reaches a consistence rate of 80%, the base type for this base in the new tested sequence was recorded as this base type, otherwise recorded as N, thereby obtaining the new tested sequence which represents the original DNA template sequence;

6) the new tested sequence was aligned again with the genome by bwa mem algorithm, and the tested sequence with an alignment quality of less than 30 was screened out;

7) statistics was carried out based on the tested sequences obtained in step 6) to obtain the base type distribution for each site, the coverage of the statistical target region, the average sequencing depth, the forward and reverse strand matching ratio, and the low-frequency mutation rate in the capture region;

8) Call SNV/InDel/SV/CNV: based on the alignment of information between the sample from a patient and a control sample, mutect process was used to call somatic SNV mutation; gatk process was used to call somatic InDel mutation; contra.py process was used to call CNV with; and som Var process was used to call SV;

the screening parameters used are: control site variation rate ≤2%; the number of varied tested sequences after error correction ≥2; mutation prediction p value ≤0.05; and 9) Mutation Annotation: the varied function, the support number of the varied tested sequence, the frequency of mutation, amino acid mutation, and the condition of such mutation in an existing mutation database are annotated.

Further, in step 1) described above, based on the sequence bases at two ends of an inserted fragment, which is a DNA fragment linked with the linker primer in the library, as tags, each fragment will form a pair of paired tested sequences by paired-end sequencing; the first 12 bp bases of tested sequence 1 and the first 12 bp bases of tested sequence 2 of paired tested sequences are taken as tags, arranged according to alphabetical order, and connected having smaller tags in the front to form an index of 24 bp; using the 24 bp as an index of the paired tested sequences, a strand is marked as a forward strand if the tag of the tested sequence 1 is in the front, and a strand is marked as a reverse strand if the tag of the tested sequence 2 is in the front.

The present invention provides a kit for enrichment and sequencing of free low-frequency mutation of free target DNA in plasma, which comprises an enrichment probe chip; the probes on the chip are provided as follows: a probe designed based on the human genome reference sequence hg19 is replaced with a probe designed based on a mutant base, and the probes for other sites are not changed; and the difference ratio between, the total coverage of probe for the hotspot mutation and the coverage of normal probe for other regions is at least 3:1;

The method for designing a probe based on a target DNA mutation base is set as follows: chip capture range is determined according to the purpose of the target gene, at least one most important hotspot mutation site is determined within a certain base range with reference to the database to which the target DNA belongs, several primary types of mutations among multiple mutation types present with respect to this site are taken for reference, corresponding frequency of occurrence is used as the proportion occupied by the mutation type in the total probe coverage level at the site.

The present invention provides a system for enrichment and sequencing of low-frequency mutation of ctDNA in plasma, which comprises the following operation units:

(1) an unit for extraction of ctDNA in plasma and library construction;

(2) an universal library TT-COLD PCR amplification and enrichment unit;

(3) a probe enrichment and capture unit, an amplification unit for hybridization capture products and an sequencing unit;

(4) an analytic unit for low-frequency information with forward and reverse double-strand error correction.

In the operation unit (1), the specific operation for extracting ctDNA in plasma and constructing library is provided as follows:

5-10 ml of peripheral blood is drawn from an early-stage patient, stored at room temperature or 4° C. in an EDTA anticoagulant tube, and separated within 4-6 hours to obtain plasma and leukocytes which will be used as a control for detection of somatic cell mutation after DNA extraction; extraction and quantitation of plasma cfDNA/ctDNA are carried out; 3-step enzymatic reaction is carried out according to conventional library construction method: terminal repair, addition of "A" and library linker ligation.

In the operation unit (2), the specific operation for universal library TT-COLD PCR amplification and enrichment is provided as follows:

based on the same instruments and reagents, fluorescence quantitative PCR is performed on normal human plasma ligation library using universal library primes, and the Tm value of the library is obtained from analysis of melting curve;

The specific Tc value present for each inserted fragment is bypassed, various mutation types of all the fragments in the library were enriched based on 1 pair of universal primers under one serial cycling condition. The method is specifically provided as follows: Tc min≈TM−2.5 is given by the empirical formula, followed by a gradual increase in Tc at a rate of 0.5° C., and FULL COLD PCR is performed under each Tc condition. PCR reaction program settings are provided as follows:

| | | |
|---|---|---|
| 98° C. | 30 sec | — |
| 98° C. | 10 sec | 3 cycles |
| 55-65° C. | 15 sec | |
| 72° C. | 30 sec | |
| 98° C. | 10 sec | 4 cycles |
| 70° C. | 2 min | |
| Tc1 = TM-2° C. | 20 sec | |
| 55-65° C. | 15 sec | |
| 72° C. | 30 sec | |
| . . . | Tc2; Tc3; Tc4 (ΔT = 0.5° C.) | 4 cycles/Tc |
| 98° C. | 10 sec | 4 cycles |
| 70° C. | 2 min | |
| Tc5 = TM-0° C. | 20 sec | |
| 55-65° C. | 15 sec | |
| 72° C. | 30 sec | |
| 72° C. | 2 min | — |
| 4° C. | Storage | —° |

The operation of the universal library TT-COLD PCR amplification and enrichment unit (2) based on a universal primer realizes the first-stage mutation enrichment and amplification for all types of mutations; the nucleotide sequences of the universal primers are:

upstream primer:
AATGATACGGCGACCACCGAGATCTACACTCTTTCCCTACACGACGCTCT

TCCGATCT, downstream primer:
CAAGCAGAAGACGGCATACGAGATxxxxxxxxGTGACTGGAGTTCAGACG

TGTGCTCTTCCGATCT, where xxxxxxxx is an index tag.

In the system for enrichment and sequencing of low-frequency mutation of ctDNA in plasma as provided in the present invention, the operation of the probe enrichment and capture unit of the unit (3) implements enrichment and capture for the second time with respect to the hotspot mutation, and is realized by using a self-designed tumor enrichment probe chip, after which amplification and sequencing are performed on the hybridization capture products. The method for designing the tumor enrichment probe chip is provided as follows:

1) the chip capture range is determined based on TCGA, ICGC, COSMIC and like databases and relevant reference documents, with reference to the design principle for conventional chip capture probes;

2) in the capture range, one most important hotspot mutation site (SNV>3) is determined within a range of 200 bp with reference to TCGA, COSMIC and other relevant databases; several primary mutation types among multiple mutation types present with respect to this site are taken for reference, and corresponding frequency of occurrence is used as the proportion occupied by the mutation type in the total probe coverage level at the site;

3) when the chip is designed, with respect to relevant hotspot mutation, a probe designed based on the human genome reference sequence hg19 is replaced with a probe designed based on a mutant base, the probes for other sites are maintained unchanged, and the difference ratio between the total coverage of the probe for hotspot mutation and the coverage of normal probe for other regions is at least 3:1, so as to achieve enrichment of hotspot mutation during capture.

In the system for enrichment and sequencing of low-frequency mutation of ctDNA in plasma as provided in the present invention, the operation of the analytic unit for low-frequency information with forward and reverse double-strand error correction (RealSeq Pipeline)(4) is completed by the following steps:

1) the first 12 bp bases of tested sequence 1 and the first 12 bp bases of tested sequence 2 of paired tested sequences are taken as tags, arranged according to alphabetical order, and connected having smaller tags in the front to form an index of 24 bp; using the 24 bp as an index of the paired tested sequences, a strand is marked as forward strand if the tag of the tested sequence 1 is in the front, and a strand is marked as reverse strand if the tag of the tested sequence 2 is in the front.

2) external sorting is carried out on the index to achieve the purpose of gathering together all the tested sequences amplified from the same DNA template;

3) center clustering is carried out on the gathered tested sequences having the same index, each large cluster with the same index is gathered into several small clusters according to the Hamming distance between the sequences, with the Hamming distance between any two pairs of paired tested sequences in each small cluster not exceeding 10, so as to achieve the purpose of distinguishing tested sequences having the same index but coming from different DNA templates;

4) the repeated clusters of the same DNA template obtained in step 3) is screened; if the numbers of tested sequences of the forward strand and the reverse strand both reach two pairs or more, subsequent analysis is performed;

5) the clusters that satisfy the conditions in 4) were corrected to generate a pair of error-free new tested sequences; for each sequenced bases in the DNA template, if a certain base type of the sequenced base in the tested sequence of the forward strand reaches a consistence rate of 80%, and in the tested sequence of the reverse strand also reaches a consistence rate of 80%, the base type for this base in the new tested sequence was recorded as this base type, otherwise recorded as N, thereby obtaining the new tested sequence which represents the original DNA template sequence;

6) the new tested sequence was aligned again with the genome by bwa mem algorithm, and the tested sequence with an alignment quality of less than 30 was screened out;

7) statistics was carried out based on the tested sequences obtained in step 6) to obtain the base type distribution for each site, the coverage of the statistical target region, the average sequencing depth, the forward and reverse strand matching ratio, and the low-frequency mutation rate in the capture region;

8) Call SNV/InDel/SV/CNV: based on the alignment of information between the sample from a patient and a control sample, mutect process was used to call somatic SNV mutation; gatk process was used to call somatic InDel mutation; contra.py process was used to call CNV with; and som Var process was used to call SV;

the screening parameters used are: control site variation rate ≤2%; the number of varied tested sequences after error correction ≥2; mutation prediction p value ≤0.05; and 9) Mutation Annotation: the varied function, the support number of the varied tested sequence, the frequency of mutation, amino acid mutation, and the condition of such mutation in an existing mutation database are annotated.

Use of the method for enrichment and sequencing of low-frequency mutations of target DNA in plasma according to the present invention or the system for enrichment and sequencing of low-frequency mutation of ctDNA in plasma as provided by the present invention, in the manufacture of a kit for early screening of a disease falls within the protection scope covered by the present invention.

The disease is a tumor.

Use of the method for enrichment and sequencing of low-frequency mutations of target DNA in plasma according to the present invention or the system for enrichment and sequencing of low-frequency mutation of ctDNA in plasma as provided by the present invention, in the manufacture of a kit for postoperative monitoring of a disease is provided.

The disease is a tumor.

Use of the method for enrichment and sequencing of low-frequency mutations of target DNA in plasma according to the present invention or the system for enrichment and sequencing of low-frequency mutation of ctDNA in plasma as provided by the present invention, in the manufacture of a kit for medication guide for a disease is provided.

The disease is a tumor.

The invention also provides an early screening chip for lung cancer, colorectal cancer, gastric cancer, breast cancer, kidney cancer, pancreatic cancer, ovarian cancer, endometrial cancer, thyroid cancer, cervical cancer, esophageal cancer and liver cancer, which is named as ONCOcare-ZS. The chip involves driver genes related with common cancers with high incidence, high frequency mutant genes, and important genes in 12 cancer-related signaling pathways, totaling 228 genes, 680 Kb, 5220 hotspot mutations. The probes contained in the chip correspond to the following genes respectively:

| ABL1 | BMPR1A | CREBBP | FAT1 | IDH2 | MITF | PCM1 | SETBP1 | VEGFA |
|---|---|---|---|---|---|---|---|---|
| ABL2 | BRAF | CRKL | FBXW7 | IGF1R | MLH1 | PDGFRA | SETD2 | VHL |
| ACVR1B | BRCA1 | CRLF2 | FGFR1 | IL7R | MLH3 | PDGFRB | SF3B1 | WT1 |
| AKT1 | BRCA2 | CSF1R | FGFR2 | INSRR | MLL2 | PHF6 | SMAD2 | XPO1 |
| AKT2 | BRD4 | CTNNB1 | FGFR3 | IRS2 | MLL3 | PIK3CA | SMAD4 | |
| AKT3 | BRIP1 | CYLD | FGFR4 | JAK1 | MPL | PIK3CB | SMARCA4 | |
| ALK | C11orf30 | DAXX | FH | JAK2 | MRE11A | PIK3R1 | SMARCB1 | |
| APC | CARD11 | DDR2 | FLCN | JAK3 | MSH2 | PMS1 | SMO | |
| AR | CASP8 | DNMT1 | FLT1 | KDM5C | MSH6 | PMS2 | SOCS1 | |
| ARAF | CBL | DNMT3A | FLT3 | KDM6A | MSR1 | PPP2R1A | SOX9 | |
| ARID1A | CCDC6 | EGFR | FLT4 | KDR | MTOR | PRDM1 | SPOP | |

-continued

| | | | | | | | |
|---|---|---|---|---|---|---|---|
| ARID1B | CCND1 | ELAC2 | FOXL2 | KIF1B | MUTYH | PTCH1 | SRC |
| ARID2 | CCND2 | EP300 | FUBP1 | KIT | MYD88 | PTEN | SRSF2 |
| ASXL1 | CCND3 | EPCAM | GAB2 | KLF4 | NBN | PTPN11 | STAG2 |
| ATM | CCNE1 | EPHA2 | GATA1 | KMT2A | NCOR1 | QC21 | STAT3 |
| ATR | CDC73 | EPHA3 | GATA2 | KMT2D | NF1 | RAD50 | STK11 |
| ATRX | CDH1 | EPHA5 | GATA3 | KRAS | NF2 | RAD51C | SYK |
| AURKA | CDK4 | ERBB2 | GNA11 | MAP2K1 | NFE2L2 | RAF1 | TERT |
| AURKB | CDK6 | ERBB3 | GNAQ | MAP2K2 | NOTCH1 | RARA | TET2 |
| AXIN1 | CDK8 | ERBB4 | GNAS | MAP3K1 | NOTCH2 | RB1 | TMEM127 |
| AXIN2 | CDKN1A | ERCC3 | H3F3A | MAPK1 | NOTCH3 | RET | TNFAIP3 |
| AXL | CDKN1B | ERG | HGF | MAX | NPM1 | RNASEL | TOP1 |
| B2M | CDKN2A | ESR1 | HIST1H3B | MCL1 | NRAS | RNF43 | TP53 |
| BAP1 | CDKN2B | EWSR1 | HNF1A | MDM2 | NTRK1 | ROS1 | TRAF7 |
| BARD1 | CEBPA | EXT1 | HRAS | MDM4 | NTRK3 | RUNX1 | TSC1 |
| BCL2 | CHEK1 | EXT2 | HSD17B3 | MED12 | PALB2 | SDHAF2 | TSC2 |
| BCOR | CHEK2 | EZH2 | HSD3B2 | MEN1 | PAX5 | SDHB | TSHR |
| BCR | CIC | FAM123B | IDH1 | MET | PBRM1 | SDHC | U2AF1 |

In one example of the present invention, early screening of tumors (lung cancer, colorectal cancer, gastric cancer, breast cancer, kidney cancer, pancreatic cancer, ovary cancer, endometrial cancer, thyroid cancer, cervical cancer, esophageal cancer and liver cancer, etc.) can be realized by the aforementioned method for enrichment and sequencing of low-frequency mutations of target DNA in plasma using the aforementioned chip of the present invention, with accurate screening results and high sensitivity, capable of realizing highly-specific detection of mutations with a low frequency of 0.01%.

The present invention also provides a probe chip for instructing individualized medication against tumor, ONCOcare-Drug, which includes: high-frequency genes of the 12 kinds of common cancer, important genes in 12 signaling pathways of cancer, common target drug and chemotherapeutic drug genes, totaling 559 genes, 850 KB, totaling 2,400 hotspot target mutations. The probes contained in the chip correspond to the following genes respectively:

| | | | | | | | | |
|---|---|---|---|---|---|---|---|---|
| ABL1 | C1R | DIS3 | FGF19 | HSPA4 | MIR142 | PAX5 | RB1 | SRSF2 |
| ABL2 | C1S | DNMT1 | FGF23 | IDH1 | MITF | PBRM1 | REL | SSTR2 |
| ACVR1B | CARD11 | DNMT3A | FGF3 | IDH2 | MLH1 | PCBP1 | RET | STAG2 |
| ACVR2A | CASP8 | DOT1L | FGF4 | IFNAR1 | MLH3 | PCM1 | RHEB | STAT4 |
| AJUBA | CBFB | DUSP6 | FGF6 | IFNAR2 | MLL | PDGFRA | RICTOR | STAT5B |
| AKT1 | CBL | EDNRA | FGF7 | IGF1 | MLL2 | PDGFRB | RNASEL | STK11 |
| AKT2 | CBLB | EGFR | FGFR1 | IGF1R | MLL3 | PDK1 | RNF43 | SUFU |
| AKT3 | CBR1 | EGR3 | FGFR2 | IGF2 | MLL4 | PHF6 | ROBO1 | SUZ12 |
| ALK | CCND1 | EIF4E2 | FGFR3 | IKBKB | MPL | PIGF | ROBO2 | SYK |
| ALOX12B | CCND2 | ELAC2 | FGFR4 | IKBKE | MRE11A | PIK3C2A | ROS1 | TAF1 |
| ANGPT1 | CCND3 | ELF3 | FH | IKZF1 | MS4A1 | PIK3C2B | RPA1 | TBL1XR1 |
| ANGPT2 | CCNE1 | EML4 | FLCN | IL7R | MSH2 | PIK3C2G | RPL22 | TBX3 |
| APC | CD79A | EP300 | FLT1 | INHBA | MSH3 | PIK3C3 | RPL5 | TEK |
| APCDD1 | CD79B | EPCAM | FLT3 | IRF4 | MSH4 | PIK3CA | RPS14 | TERT |
| AR | CDC25C | EPHA2 | FLT4 | IRS2 | MSH5 | PIK3CB | RPS6KB1 | TET2 |
| ARAF | CDC42 | EPHA3 | FNTA | ITGB2 | MSH6 | PIK3CG | RPTOR | TFG |
| ARFRP1 | CDC73 | EPHA5 | FOXA1 | JAK1 | MSR1 | PIK3R1 | RUNX1 | TGFBR2 |
| ARHGAP35 | CDH1 | EPHB1 | FOXA2 | JAK2 | MTOR | PIK3R2 | RUNX1T1 | TIPARP |
| ARID1A | CDK12 | EPHB2 | FOXL2 | JAK3 | MUC1 | PLK1 | RXRA | TLR4 |
| ARID1B | CDK2 | EPHB6 | FPGS | JUN | MUTYH | PML | RXRB | TMEM127 |
| ARID2 | CDK4 | EPPK1 | FUBP1 | KAT6A | MYC | PMS1 | RXRG | TNFAIP3 |
| ARID5B | CDK6 | ERBB2 | FYN | KDM5A | MYCL1 | PMS2 | SDHAF2 | TNFRSF14 |
| ASXL1 | CDK8 | ERBB3 | GAB2 | KDM5C | MYCN | PNRC1 | SDHB | TNFRSF8 |
| ATM | CDKN1A | ERBB4 | GATA1 | KDM6A | MYD88 | POLQ | SDHC | TNFSF11 |
| ATR | CDKN1B | ERCC2 | GATA2 | KDR | NAV3 | PPP2R1A | SDHD | TNFSF13B |
| ATRX | CDKN2A | ERCC3 | GATA3 | KEAP1 | NBN | PRDM1 | SEMA3A | TOP1 |
| AURKA | CDKN2B | ERG | GID4 | KIF1B | NCOA1 | PRKAA1 | SEMA3E | TOP2A |
| AURKB | CDKN2C | ESR1 | GNA11 | KIF5B | NCOA2 | PRKAR1A | SETBP1 | TOP2B |
| AXIN1 | CDX2 | ETV1 | GNA13 | KIT | NCOR1 | PRKCA | SETD2 | TP53 |
| AXIN2 | CEBPA | ETV6 | GNAQ | KLF4 | NEK11 | PRKCB | SF1 | TRAF7 |
| AXL | CFLAR | EWSR1 | GNAS | KLHL6 | NF1 | PRKCG | SF3B1 | TSC1 |
| B2M | CHD1 | EXT1 | GNRHR | KRAS | NF2 | PRKDC | SH2B3 | TSC2 |
| B4GALT3 | CHD2 | EXT2 | GPR124 | LCK | NFE2L2 | PRSS8 | SIN3A | TSHR |
| BACH1 | CHD4 | EZH2 | GRIN2A | LIMK1 | NFE2L3 | PSMB1 | SLAMF7 | TSHZ2 |

-continued

| | | | | | | | | | |
|---|---|---|---|---|---|---|---|---|---|
| BAK1 | CHEK1 | FAM123B | GRM3 | LRRK2 | NFKBIA | PSMB2 | SLC4A1 | TSHZ3 | |
| BAP1 | CHEK2 | FAM46C | GSK3B | LYN | NKX2-1 | PSMB5 | SLIT2 | TUBA1A | |
| BARD1 | CHUK | FANCA | H3F3A | MALAT1 | NKX3-1 | PTCH1 | SMAD2 | TUBB | |
| BCL2 | CIC | FANCC | H3F3C | MAP2K1 | NOTCH1 | PTCH2 | SMAD3 | TUBD1 | |
| BCL2A1 | CRBN | FANCD2 | HCK | MAP2K2 | NOTCH2 | PTEN | SMAD4 | TUBE1 | |
| BCL2L1 | CREBBP | FANCE | HDAC1 | MAP2K4 | NOTCH3 | PTP4A3 | SMARCA1 | TUBG1 | |
| BCL2L11 | CRIPAK | FANCF | HDAC2 | MAP3K1 | NOTCH4 | PTPN11 | SMARCA4 | TYR | |
| BCL2L2 | CRKL | FANCG | HDAC3 | MAP3K13 | NPM1 | PTPRD | SMARCB1 | U2AF1 | |
| BCL6 | CRLF2 | FANCI | HDAC4 | MAPK1 | NR3C1 | RAC1 | SMARCD1 | USP9X | |
| BCOR | CROT | FANCL | HDAC6 | MAPK3 | NRAS | RAC2 | SMC1A | VEGFA | |
| BCORL1 | CSF1R | FANCM | HDAC8 | MAPK8 | NSD1 | RAD21 | SMC3 | VEGFB | |
| BCR | CTCF | FAT3 | HGF | MAPK8IP1 | NTRK1 | RAD50 | SMO | VEZF1 | |
| BLM | CTLA4 | FBXW7 | HIF1A | MAX | NTRK2 | RAD51 | SOCS1 | VHL | |
| BMPR1A | CTNNA1 | FCGR1A | HIST1H1C | MC1R | NTRK3 | RAD51B | SOX10 | WHSC1L1 | |
| BRAF | CTNNB1 | FCGR2A | HIST1H2BD | MCL1 | NUP93 | RAD51C | SOX17 | WISP3 | |
| BRCA1 | CUL4A | FCGR2B | HIST1H3B | MDM2 | PAK3 | RAD51D | SOX2 | WWP1 | |
| BRCA2 | CUL4B | FCGR2C | HNF1A | MDM4 | PAK7 | RAD52 | SOX9 | XIAP | |
| BRIP1 | CYLD | FCGR3A | HRAS | MECOM | PALB2 | RAD54L | SPEN | XPA | |
| BTG1 | CYP17A1 | FCGR3B | HRH2 | MED12 | PARP1 | RAF1 | SPOP | XPC | |
| BTK | DAXX | FGF10 | HSD17B3 | MEF2B | PARP2 | RARA | SPRY4 | XPO1 | |
| C11orf30 | DDR1 | FGF12 | HSD3B2 | MEN1 | PARP3 | RARB | SRC | XRCC3 | |
| C1QA | DDR2 | FGF14 | HSP90AA1 | MET | PARP4 | RARG | SRD5A2 | YES1 | |
| ZNF217 | ZNF703 | ZRSR2 | WT1 | XRCC1 | GSTP1 | ERCC1 | MTHFR | SOD2 | |
| UMPS | UGT1A1 | CBR3 | ATIC | MTRR | DPYD | TPMT | | | |

In one example of the present invention, individualized medication guide against 12 kinds of common tumors (lung cancer, colorectal cancer, gastric cancer, breast cancer, kidney cancer, pancreatic cancer, ovary cancer, endometrial cancer, thyroid cancer, cervical cancer, esophageal cancer and liver cancer, etc.) can be realized by the aforementioned method for enrichment and sequencing of low-frequency mutations of target DNA in plasma using the aforementioned chip of the present invention, with definite therapeutic effect.

The present invention also provides a chip for postoperative monitoring of tumors (lung cancer, colorectal cancer, gastric cancer, breast cancer, kidney cancer, pancreatic cancer, ovary cancer, endometrial cancer, thyroid cancer, cervical cancer, esophageal cancer and liver cancer, etc.), ONCOcare-JK, which includes: Driver Genes related with common cancers with high incidence, high-frequency mutant genes, important genes in 12 cancer-related signaling pathways, totaling 508 genes, 500 Kb, 4,800 hotspot mutations. The probes contained in the chip correspond to the following genes respectively:

| | | | | | | | | |
|---|---|---|---|---|---|---|---|---|
| ABL1 | CBLB | DOT1L | FGF7 | IGF2 | MSH2 | PIK3CB | SDHB | TRAF7 |
| ABL2 | CBR1 | DUSP6 | FGFR1 | IKBKB | MSH3 | PIK3CG | SDHC | TSC1 |
| ACVR1B | CCND1 | EDNRA | FGFR2 | IKBKE | MSH4 | PIK3R1 | SDHD | TSC2 |
| ACVR2A | CCND2 | EGFR | FGFR3 | IKZF1 | MSH5 | PIK3R2 | SEMA3A | TSHR |
| AJUBA | CCND3 | EGR3 | FGFR4 | IL7R | MSH6 | PLK1 | SEMA3E | TSHZ2 |
| AKT1 | CCNE1 | EIF4A2 | FLCN | INHBA | MSR1 | PML | SETBP1 | TSHZ3 |
| AKT2 | CD79A | ELAC2 | FLT1 | IRF4 | MTOR | PMS1 | SETD2 | TUBA1A |
| AKT3 | CD79B | ELF3 | FLT3 | IRS2 | MUC1 | PMS2 | SF1 | TUBB |
| ALK | CDC25C | EML4 | FLT4 | ITGB2 | MUTYH | PNRC1 | SF3B1 | TUBD1 |
| ANGPT1 | CDC42 | EP300 | FNTA | JAK1 | MYC | POLQ | SH2B3 | TUBE1 |
| ANGPT2 | CDC73 | EPHA2 | FOXA1 | JAK2 | MYCL1 | PPP2R1A | SIN3A | TUBG1 |
| APC | CDH1 | EPHA3 | FOXA2 | JAK3 | MYCN | PRDM1 | SLAMF7 | TYR |
| AR | CDK12 | EPHA5 | FOXL2 | JUN | NAV3 | PRKCA | SLC4A1 | VEGFA |
| ARAF | CDK2 | EPHB1 | FPGS | KDR | NBN | PRKCB | SLIT2 | VEGFB |
| ARFRP1 | CDK4 | EPHB2 | FUBP1 | KEAP1 | NCOA1 | PRKCG | SMAD2 | VEZF1 |
| ARID1A | CDK6 | EPHB6 | FYN | KIF1B | NCOA2 | PRKDC | SMAD3 | VHL |
| ARID1B | CDK8 | EPPK1 | GAB2 | KIF5B | NCOR1 | PRSS8 | SMAD4 | WISP3 |
| ASXL1 | CDKN1A | ERBB2 | GATA1 | KIT | NEK11 | PSMB1 | SMARCA1 | WT1 |
| ATM | CDKN1B | ERBB3 | GATA2 | KLF4 | NF1 | PSMB2 | SMC1A | WWP1 |
| ATR | CDKN2A | ERBB4 | GATA3 | KLHL6 | NF2 | PSMB5 | SMC3 | XIAP |
| ATRX | CDKN2B | ERCC2 | GID4 | KRAS | NOTCH1 | PTCH1 | SMO | XPA |
| AURKA | CDKN2C | ERCC3 | GNA11 | LCK | NOTCH2 | PTCH2 | SOCS1 | XPC |
| AURKB | CDX2 | ERG | GNA13 | LIMK1 | NOTCH3 | PTEN | SOX2 | XPO1 |
| AXIN1 | CEBPA | ESR1 | GNAQ | LRRK2 | NOTCH4 | PTP4A3 | SOX9 | XRCC3 |
| AXIN2 | CFLAR | ETV1 | GNAS | MALAT1 | NPM1 | PTPN11 | SPEN | YES1 |
| AXL | CHD1 | ETV6 | GNRHR | MAP2K1 | NR3C1 | PTPRD | SPRY4 | ZNF217 |

-continued

| | | | | | | | | |
|---|---|---|---|---|---|---|---|---|
| BACH1 | CHD2 | EWSR1 | GPR124 | MAP2K2 | NRAS | RAC1 | SRC | ZRSR2 |
| BAK1 | CHD4 | EXT1 | GRIN2A | MAP2K4 | NSD1 | RAC2 | SRD5A2 | |
| BAP1 | CHEK1 | EXT2 | GRM3 | MAP3K1 | NTRK1 | RAD21 | SRSF2 | |
| BARD1 | CHEK2 | EZH2 | GSK3B | MAP3K13 | NTRK2 | RAD50 | SSTR2 | |
| BCL2 | CHUK | FAM46C | H3F3A | MAPK1 | NTRK3 | RAD51 | STAG2 | |
| BCL2A1 | CIC | FANCA | H3F3C | MAPK3 | NUP93 | RAF1 | STAT4 | |
| BCL2L1 | CRBN | FANCC | HCK | MAPK8 | PAK3 | RARA | STAT5B | |
| BCL2L2 | CREBBP | FANCD2 | HDAC1 | MAX | PAK7 | RARB | STK11 | |
| BCL6 | CRIPAK | FANCE | HDAC2 | MC1R | PALB2 | RARG | SUFU | |
| BCOR | CRKL | FANCF | HDAC3 | MCL1 | PARP1 | RB1 | SUZ12 | |
| BCORL1 | CRLF2 | FANCG | HDAC4 | MDM2 | PARP2 | REL | SYK | |
| BCR | CTCF | FANCI | HDAC6 | MDM4 | PARP3 | RET | TAF1 | |
| BLM | CTLA4 | FANCL | HDAC8 | MED12 | PARP4 | RHEB | TBX3 | |
| BMPR1A | CTNNA1 | FANCM | HGF | MEF2B | PCM1 | RNF43 | TEK | |
| BRAF | CTNNB1 | FAT3 | HIF1A | MEN1 | PDGFRA | ROBO1 | TERT | |
| BRCA1 | CUL4A | FBXW7 | HNF1A | MET | PDGFRB | ROBO2 | TET2 | |
| BRCA2 | CUL4B | FCGR2A | HRAS | MITF | PDK1 | ROS1 | TFG | |
| BRIP1 | CYLD | FCGR2B | HRH2 | MLH1 | PHF6 | RPA1 | TGFBR2 | |
| BTG1 | DAXX | FCGR2C | IDH1 | MLH3 | PIGF | RPL5 | TIPARP | |
| BTK | DDR1 | FCGR3A | IDH2 | MLL | PIK3C2A | RPS14 | TLR4 | |
| CARD11 | DDR2 | FCGR3B | IFNAR1 | MLL2 | PIK3C2B | RXRA | TOP1 | |
| CASP8 | DIS3 | FGF3 | IFNAR2 | MLL3 | PIK3C2G | RXRB | TOP2A | |
| CBFB | DNMT1 | FGF4 | IGF1 | MLL4 | PIK3C3 | RXRG | TOP2B | |
| CBL | DNMT3A | FGF6 | IGF1R | MS4A1 | PIK3CA | SDHAF2 | TP53 | |

In one example of the present invention, postoperative monitoring of 12 kinds of common tumors (lung cancer, colorectal cancer, gastric cancer, breast cancer, kidney cancer, pancreatic cancer, ovary cancer, endometrial cancer, thyroid cancer, cervical cancer, esophageal cancer and liver cancer, etc.) can be realized by the aforementioned method for enrichment and sequencing of low-frequency mutations of target DNA in plasma using the aforementioned chip of the present invention, and estimation of whether or not recurrent risk is present in patients after operation can be monitored accurately.

The present invention provides a method for enrichment and sequencing of low-frequency mutations of target DNA in plasma (ER-seq, Enrich & Rare mutation Sequencing), which combines 3 techniques, i.e. universal library TT-COLD PCR, probe enrichment capture and unique information analysis technique by forward and reverse strand error correction (RealSeq Pipeline), and realize high-efficiency, convenient and practicable accurate detection of low-frequency mutations of ctDNA in plasma. Compared with other plasma detecting techniques, the present invention has the following excellent effects: (1) high sensitivity: ER-Seq uses particular universal library TT-COLD PCR and probe enrichment and capture technique to enable enrichment of all mutation types and hotspot mutations at different degrees; therefore, only 5-10 mL of peripheral blood sample is needed, and rare mutation at a frequency of 0.01% can be detected with high efficiency; (2) high specificity: based on enrichment of mutations and analysis strategy of low-frequency forward and reverse strand error-correction, the accurate detection of low-frequency mutations can be more effectively achieved with a specificity of 98% or greater; (3) high-throughput: the target region capture sequencing combining with high-throughput sequencing (NGS) can not only scanning relevant genes of interest at once for obtaining more comprehensive information of the subject to make more accurate prediction, but also detect multiple samples simultaneously in a very short period of time, so as to reduce costs and facilitate clinical promotion; (4) multidimensional applicability: this method can fully exploit the potential of plasma ctDNA, and lays a solid foundation for early screening, postoperative monitoring and accurate medical treatment of a variety of related tumors (lung cancer, colorectal cancer, gastric cancer, breast cancer, kidney cancer, pancreatic cancer, ovarian cancer, endometrial cancer, thyroid cancer, cervical cancer, esophageal cancer and liver cancer, etc.), so as to give a big push to the development of clinical oncology.

BEST MODE OF THE INVENTION

Figure 1:
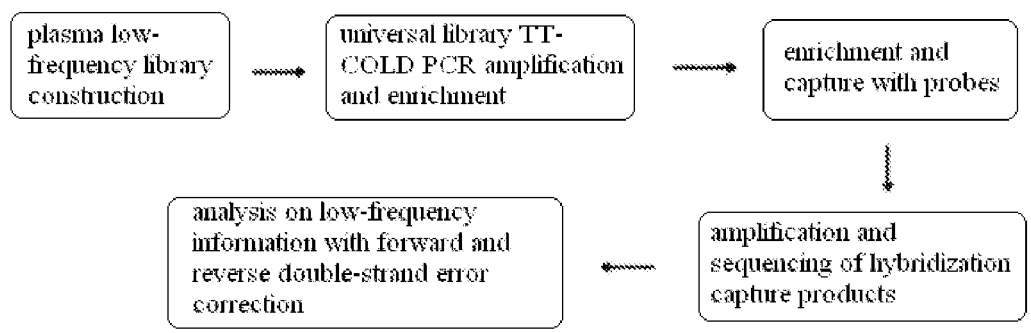
FIG. 1 is a process chart of the method of the present invention.

The following examples further illustrate the present invention, but should not be construed as limitation to the present invention. Any modification or substitution of the methods, steps or conditions of the present invention without departing from the spirit and essence of the present invention all fall within the scope of the present invention.

Unless otherwise specified, all the chemical reagents used in the examples are conventional commercially-available reagents. The technical means used in the examples are conventional ones known to those skilled in the art. The sequencing device used in the examples of the present invention is the Illumina HiSeq2500. In the sequencing step of the present invention, the sequencing device is not limited to the above sequencing device.

In the examples of the present invention, all gene names adopt official symbols in NCBI-Gene. The synonymous mutation in the present invention means that the codon representing an amino acid is mutated to other codons due to a change of a certain base, but said other codons still encode the same amino acid. Missense mutation means that a codon encoding a certain amino acid becomes a codon encoding another amino acid after substitution of a base, so that the type of amino acids and the sequence of the polypeptide chain are changed. Some missense mutations can make the polypeptide chain lose its original function, and many protein abnormalities are caused by missense mutations. a mutation resulting in a termination codon, also referred to as nonsense mutation, means that a codon representing an amino acid is mutated to a termination codon due to a change of a certain base, so that the synthesis of a peptide chain is terminated in advance. A mutation resulting in the loss of a termination codon according to the present invention means that a termination codon is mutated to other codons due to a change of a certain base, so that the synthesis of a peptide chain cannot be terminated normally.

Example 1 Method for Enrichment and Sequencing of Low-Frequency Mutations of Target DNA in Plasma (ER-Seq Method)

(1) Extraction of target DNA from plasma and construction of a library. The plasma was derived from human peripheral blood and the method for library construction was performed according to a three-step enzymatic reaction, i.e. terminal repair, addition of "A" and library linker ligation. The primers for the library linker were provided as follows:

The first strand of the linker: TACACTCTTTCCCTA-CACGACGCTCTTCCGATCT,

The second strand of the linker: GATCG-GAAGAGCACACGTCTGAACTCCAGTCAC.

(2) Universal library TT-COLD PCR amplification and enrichment. It comprised the following steps:

1) determining the Tm value of the library; the Tm value of the library was determined by the following method: fluorescence quantitative PCR was performed on the library of the target DNA in plasma using one pair of primers, and analysis was carried out according to melting curve to obtain the Tm value of the library; the sequence of the primers were provided as follows:

upstream primer:
AATGATACGGCGACCACCGAGATCTA-CACTCTTTCCCTACACGACGCTCTTCCGA TCT, and
downstream primer:
CAAGCAGAAGACGGCAT-ACGAGATxxxxxxxxGTGACTGGAGTTCA-GACGTGTGC TCTTCCGATCT, wherein, xxxxxxxx is an index tag;

2) bypassing specific Tc values present for each inserted fragment, enriching various types of mutations on all fragments in the library based on one pair of universal primers under one serial cycling condition; setting Tc min≈TM−2.5, followed by a gradual increase in Tc at a rate of 0.5° C., and performing FULL COLD PCR under each Tc condition, respectively;

the one pair of universal primers was universal library TT-COLD PCR primer, and its nucleotide sequence was: upstream primer: AATGATACGGCGACCACCGAGATC-TACACTCTTTCCCTACACGACGCTCTTCCGATCT, and downstream primer: CAAGCAGAAGACGGCAT-ACGAGATxxxxxxxxGTGACTGGAGTTCA-GACGTGTGCTCT TCCGATCT, wherein, xxxxxxxx was an index tag;

the one serial cycling condition was:

| | | |
|---|---|---|
| 98° C. | 30 sec | — |
| 98° C. | 10 sec | 3 cycles |
| 55-65° C. | 15 sec | |
| 72° C. | 30 sec | |
| 98° C. | 10 sec | 4 cycles |
| 70° C. | 2 min | |
| Tc1 = TM−2° C. | 20 sec | |
| 55-65° C. | 15 sec | |
| 72° C. | 30 sec | |
| . . . | Tc2; Tc3; Tc4 (ΔT = 0.5° C.) | 4 cycles/Tc |

-continued

| | | |
|---|---|---|
| 98° C. | 10 sec | 4 cycles |
| 70° C. | 2 min | |
| Tc5 = TM−0° C. | 20 sec | |
| 55-65° C. | 15 sec | |
| 72° C. | 30 sec | |
| 72° C. | 2 min | — |
| 4° C. | Storage | —. |

(3) Enrichment and capture with probes, and amplification and sequencing of products captured by hybridization, The enrichment and capture with probes in step (3) referred to using an enrichment probe chip for capture via hybridization after the amplified library was qualified in quality control, and the products captured by hybridization were subjected to PCR amplification and then on-machine sequencing;

the design method for the enrichment probe chip was set as follows: the capture range of the chip was determined based on the purpose of the target gene, at least one most important hotspot mutation site was determined within a certain base range with reference to the database to which the target DNA belongs, several primary types of mutations among multiple mutation types present at this site were taken for reference, corresponding frequency of occurrence was used as the proportion occupied by the mutation type in the total probe coverage level at the site; with respect to the hotspot mutation, a probe designed based on a human genome reference sequence hg19 was replaced with a probe designed based on a mutant base, the probes for other sites were maintained unchanged, and the difference ratio between the total coverage of the probe for hotspot mutation and the coverage of the normal probe for other regions was not less than 3:1, so as to achieve enrichment of hotspot mutation during capture.

(4) The specific method for analysis on low-frequency information with forward and reverse double-strand error correction (RealSeq Pipeline) was provided as follows:

1) based on the sequence bases at two ends of an inserted fragment, (which was a DNA fragment linked with the linker primer in the library) as tags, each fragment formed a pair of paired tested sequences by paired-end sequencing; the first 12 bp bases of tested sequence 1 and the first 12 bp bases of tested sequence 2 of the paired tested sequences were taken as tags, arranged according to alphabetical order, and connected having smaller tags in the front to form an index of 24 bp; using the 24 bp as an index of the paired tested sequences, the strand was marked as a forward strand if the tag of the tested sequence 1 is in the front, and strand was marked as a reverse strand if the tag of the tested sequence 2 is in the front;

2) external sorting was carried out on the index to achieve the purpose of gathering together all the tested sequences of the same DNA template;

3) center clustering was carried out on the gathered tested sequences having the same index, each large cluster with the same index was gathered into several small clusters according to the Hamming distance between the sequences, with the Hamming distance between any two pairs of paired tested sequences in each small cluster not exceeding 10, so as to achieve the purpose of distinguishing tested sequences having the same index but coming from different DNA templates;

4) repeated clusters of the same DNA template obtained in step 3) was screened; if the numbers of tested sequences of the forward strand and the reverse strand both reached two pairs or more, subsequent analysis was performed;

5) the clusters that satisfy the conditions in 4) were corrected to generate a pair of error-free new tested sequences; for each sequenced base in the DNA template, if a certain base type of the sequenced base in the tested sequence of the forward strand reached a consistence rate of 80%, and in the tested sequence of the reverse strand also reached a consistence rate of 80%, the base type for this base in a new tested sequence was recorded as this base type, otherwise recorded as N, thereby obtaining the new tested sequence which represents the original DNA template sequence;

6) the new tested sequence was aligned again with the genome by bwa mem algorithm, and the tested sequence with an alignment quality of less than 30 was screened out;

7) statistics was carried out based on the tested sequences obtained in step 6) to obtain the base type distribution for each site, the coverage of the statistical target region, the average sequencing depth, the forward and reverse strand matching ratio, and the low-frequency mutation rate in the capture region;

8) Call SNV/InDel/SV/CNV: based on the alignment of information between the sample from a patient and a control, the mutect process was used to call somatic SNVmutation; the gatk process was used to call somatic InDel mutation; the contra.py process was used to call CNV with; and the som Var process was used to call SV;

the screening parameters used were: control site mutation rate ≤2%; the number of varied tested sequences after error correction ≥2; mutation prediction p value ≤0.05; and 9) Mutation Annotation: the varied function, the support of the varied tested sequence, the frequency of mutation, amino acid mutation, and the condition of such mutation in an existing mutation database were annotated.

Example 2 Establishment of Enrichment and Sequencing Method for Low Frequency Mutation of ctDNA in Plasma 1. Extraction of ctDNA from Plasma and Library Construction (1) 1-2 tubes (5 mL/tube) of the peripheral blood was drawn from the subject into an EDTA anticoagulant tube, gently shaken upside down (to prevent cell rupture) 6-8 times to mix thoroughly, and subjected to the following treatment within 4-6 hours on the day of blood sampling: the sample was centrifuged at 4° C. and 1600 g for 10 minutes; after centrifugation, the supernatant (plasma) was dispensed into a plurality of 1.5 mL/2 mL centrifuge tubes, and the middle layer of leukocytes could not be sucked during the sucking; centrifugation was carried out at 4° C. and 1600 g for 10 minutes, the remaining cells were removed, and the supernatant (plasma) was transferred to a new 1.5 mL/2 mL centrifuge tube, during which process the leukocytes at the bottom of the tube could not be sucked, to obtain the desired separated plasma; after treatment of plasma samples was finished, the resulting plasma and remaining blood cells were stored in a refrigerator at −80° C. to avoid repeated freezing and thawing.

(2) Extraction and quantitation of plasma cfDNA/ctDNA: approximately 2-3 ml of the separated plasma was taken, and plasma cfDNA was extracted therefrom according to the extracting reagent instruction of QIAamp Circulating Nucleic Acid Kit (Qiagen). The extracted DNA was quantified by Qubit (Invitrogen, the Quant-iT™ dsDNA HS Assay Kit), and the total amount was about 30-50 ng.

(3) Preparation of a library of the sample: the cfDNA extracted from plasma was subjected to 3-step enzymatic reaction according to the instruction for library construction of KAPA LTP Library Preparation Kit.

3.1 Terminal Repair

| DNA sample | 50 μL |
| Terminal repair pre-mixed solution | 20 μL |
| water | 8 μL |
| 10 × KAPA terminal repair buffer | 7 μL |
| KAPA terminal repair enzyme mixture | 5 μL |
| total volume | 70 μL |

The materials were mixed well and incubated at 20° C. for 30 min.

After that, 120 μL of Agencourt AMPure XP reagent was added, and the mixture was purified with beads, and finally dissolved in 42 μL of ddH$_2$O, and subjected to the next step of reaction with the beads.

3.2 Addition of A

| A-tailing reaction pre-mixed solution: | 50 μL |
| water + DNA | 42 μL |
| 10 × KAPA A-Tailing Buffer(Blue) (A-tailing reaction buffer) | 5 μL |
| KAPA A-Tailing Enzyme(Blue) (enzyme for A-tailing reaction) | 3 μL |
| Total volume | 50 μL |

The materials were mixed well and incubated at 30° C. for 30 min

After that, 90 μL of PEG/NaCl SPRI solution was added, and mixed thoroughly; and the mixture was purified with beads, and finally dissolved in (35-linker)μL of ddH$_2$O, and subjected to the next step of reaction with the beads.

3.3 Linker Ligation

| Ligation pre-mixed solution | 45 μL |
| water | (35-linker) μL |
| 5 × KAPA ligation buffer | 10 μL |
| KAPA T4 DNA ligase | 5 μL |
| 15 μM linker(50:1) | final concentration 10 nM/ng |
| Total volume | 50 μL |

The materials were mixed well and incubated at 16° C. for 16 hours.

With respect to the linker primer, please refer to Table 1 for the first and second strands of the linker. After that, 50 μL of PEG/NaCl SPRI solution was added twice, and the mixture was purified with beads twice, and finally dissolved in 25 μL of ddH$_2$O.

Figure 2:
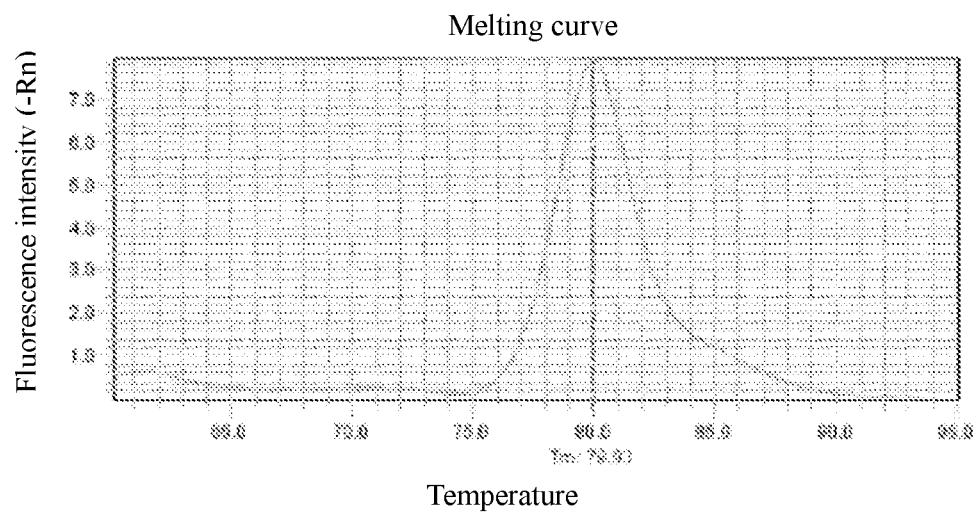
FIG. 2 shows the Tm values of normal human plasma ligation libraries.

2. Universal Library TT-COLD PCR:

1) Fluorescent quantitative PCR was performed using universal library primers for normal human plasma ligation libraries based on the same instruments and reagents, and the reaction reagents included KAPA HiFi HotStart ReadyMix and SYBR dye. By analysis of the melting curve, the Tm value (DNA melting temperature) of the library was obtained, as shown in FIG. 2. The universal library primer is shown in Table 1.

TABLE 1

Primer sequence information

| primer | Sequence information (5'-3') |
|---|---|
| First strand of the linker | TACACTCTTTCCCTACACGACGCTCTTCCGATCT |
| Second strand of the linker | GATCGGAAGAGCACACGTCTGAACTCCAGTCAC |
| Universal library upstream primer | AATGATACGGCGACCACCGAGATCTACACTCTTTCCCT ACACGACGCTCTTCCGATCT |
| Universal library downstream primer | CAAGCAGAAGACGGCATACGAGATxxxxxxxxGTGACTG GAGTTCAGACGTGTGCTCTTCCGATCT |

Note:
xxxxxxxx: index tag

2) Universal Library TT COLD PCR: the reaction system was:

| Plasma ctDNA ligation library: | 20 μL |
|---|---|
| 2 × KAPA HiFi HotStart Ready Mix | 25 μL |
| 10 μM universal library upstream primer | 2.5 μL |
| 10 μM universal library downstream primer | 2.5 μL |
| Total volume | 50 μL |

The above materials were mixed well.

By bypassing the specific Tc values present for each inserted fragment, various mutations on all the fragments in the library were enriched based on the 1 pair of universal library primers shown in Table 1 under 1 serial cycling condition. Specifically, the method was obtaining Tc min≈TM−2.5 by an empirical formula, followed by a gradual increase in Tc at a rate of 0.5° C., and FULL COLD PCR was performed under each Tc condition. PCR reaction program settings are shown in Table 2.

TABLE 2

| | 98° C. | 30 sec | — |
|---|---|---|---|
| | 98° C. | 10 sec | 3 cycles |
| | 55-65° C. | 15 sec | |
| | 72° C. | 30 sec | |
| | 98° C. | 10 sec | 4 cycles |
| | 70° C. | 2 min | |
| Tc1 = TM−2° C. | | 20 sec | |
| | 55-65° C. | 15 sec | |
| | 72° C. | 30 sec | |
| ... | | Tc2; Tc3; Tc4 (ΔT = 0.5° C.) | 4 cycles/Tc |
| | 98° C. | 10 sec | 4 cycles |
| | 70° C. | 2 min | |
| Tc5 = TM−0° C. | | 20 sec | |
| | 55-65° C. | 15 sec | |
| | 72° C. | 30 sec | |
| | 72° C. | 2 min | — |
| | 4° C. | Storage | — |

3. Enrichment and Capture with Probes and On-Machine Sequencing

1) Design of Enrichment Probe Chip for Tumor:

The capture range of the chip was determined based on TCGA, ICGC, COSMIC and like databases and relevant reference documents, with reference to the design principle for conventional capture probes for chips;

In the capture range, at least one most important hotspot mutation site (SNV>3) was determined for each 200 bps with reference to TCGA, COSMIC and other relevant databases; several primary mutation types among multiple mutation types present at this site were taken for reference, and corresponding frequency of occurrence was used as the proportion occupied by the mutation type in the total probe coverage level at the site;

When the chip was designed, with respect to relevant hotspot mutation, a probe designed based on REF was replaced with a probe designed based on a mutant base, other probes were maintained unchanged, and the difference ratio between the total coverage of the probe for hotspot mutation and the coverage of normal probe for other regions was at least 3:1, so as to achieve enrichment of hotspot mutation during capture.

2) After amplification, library was subjected to quality control and enrichment-probe capture, followed by amplification and on-machine sequencing of products captured via hybridization.

After the amplified library was qualified in quality control, the above enrichment probe chips for tumor were used for capture via hybridization according to the instructions provided by the chip manufacturer (Roche). Finally, the resulting material was eluted and dissolved in 21 μL ddH$_2$O, with beads subjected to hybridization and elution.

Amplification System for Products Captured Via Hybridization:

| Products captured via hybridization | 20 μL |
|---|---|
| 2 × KAPA HiFi HotStart Ready Mix | 25 μL |
| FellowCell Primer 1 | 2.5 μL |
| FellowCell Primer 2 | 2.5 μL |
| Total volume | 50 μL |

PCR reaction conditions: initial denaturation at 98° C. for 45 sec; denaturation at 98° C. for 15 sec, annealing at 65° C. for 30 sec, extension at 72° C. for 30 sec, totaling 10 cycles; extension at 72° C. for 60 sec, storage at 4° C.

FellowCell Primer 1 and Primer 2 were primers contained in the Hiseq on-machine test platform, which were used for amplifying the captured DNA template to obtain enough output to meet the requirements of on-machine sequencing.

The beads from the previous step were removed first, and then 50 μL of Agencourt AMPure XP reagent was added again. The mixture was purified with beads, and finally dissolved in 25 μL ddH$_2$O and subjected to QC and on-machine sequencing. Illumina HiSeq 2500 PE101+8+101 program was used for on-machine sequencing. In sequencing experimental operation, operations for on-machine sequencing were carried out according to the manufacturer's instructions (see cBot officially published by Illumina/Solexa).

4. Analysis on Low-Frequency Information with Forward and Reverse Double-Strand Error Correction (RealSeq Pipeline Method):

1) based on the sequence bases at two ends of an inserted fragment (which was a DNA fragment linked with the linker primer in the library) as tags, each fragment formed a pair of paired tested sequences by paired-end sequencing; the first 12 bp bases of tested sequence 1 and the first 12 bp bases of tested sequence 2 of paired tested sequences were taken as tags, arranged according to alphabetical order, and connected having smaller tags in the front to form an index of 24 bp; using the 24 bp as an index of the paired tested sequences, a strand was marked as a forward strand if the tag of the tested sequence 1 is in the front, and a strand was marked as a reverse strand if the tag of the tested sequence 2 is in the front;

2) external sorting was carried out on the index to achieve the purpose of gathering together all the tested sequences amplified from the same DNA template;

3) center clustering was carried out on the gathered tested sequences having the same index, each large cluster with the same index was gathered into several small clusters according to the Hamming distance between the sequences, with the Hamming distance between any two pairs of paired tested sequences in each small cluster not exceeding 10, so as to achieve the purpose of distinguishing tested sequences having the same index but coming from different DNA templates;

4) repeated clusters of the same DNA template obtained in step 3) was screened; if the numbers of tested sequences of the forward strand and the reverse strand both reached two pairs or more, subsequent analysis was performed;

5) the clusters that satisfy the conditions in 4) were corrected to generate a pair of error-free new tested sequences; for each sequenced base in the DNA template, if a certain base type for the base in the tested sequence of the forward strand reached a consistence rate of 80%, and in the tested sequence of the reverse strand also reached a consistence rate of 80%, the base type for this base in a new tested sequence was recorded as this base type, otherwise recorded as N, thereby obtaining the new tested sequence which represents the original DNA template sequence;

6) the new tested sequence was aligned again with the genome by bwa mem algorithm, and the tested sequence with an alignment quality of less than 30 was screened out;

7) statistics was carried out based on the tested sequences obtained in step 6) to obtain the base type distribution for each site, the coverage of the statistical target region, the average sequencing depth, the forward and reverse strand matching ratio, and the low-frequency mutation rate in the capture region;

8) Call SNV/InDel/SV/CNV: based on the alignment of information between the sample from a patient and a control sample, the mutect process was used to call somatic SNV mutation; the gatk flow was used to call somatic InDel mutation; the contra.py flow was used to call CNV with; and the som Var flow was used to call SV;

the screening parameters used were: mutation rate for a control site ≤2%; the number of varied tested sequences after error correction ≥2; mutation prediction p value ≤0.05; and 9) Mutation Annotation: the varied function, the support number of the varied tested sequence, the frequency of mutation, amino acid mutation, and the condition of such mutation in an existing mutation database were annotated.

Example 3 Early Screening of Tumor

1. Chip Design

A chip, ONCOcare-ZS, for early screening of tumors (lung cancer, colorectal cancer, gastric cancer, breast cancer, kidney cancer, pancreatic cancer, ovarian cancer, endometrial cancer, thyroid cancer, cervical cancer, esophageal cancer and liver cancer, etc.) was completed based on the design principle of enrichment probe chips. The chip includes Driver Genes related with common cancers with high incidence, high-frequency mutation genes, important genes in 12 cancer-related signaling pathways, totaling 227 genes, 680 Kb, 5220 hotspot mutation. The gene list is shown in Table 3.

TABLE 3

Gene list of the early-screening chip ONCOcare-ZS

| ABL1 | BMPR1A | CREBBP | FAT1 | IDH2 | MLH1 | PDGFRA | SETD2 | VHL |
|---|---|---|---|---|---|---|---|---|
| ABL2 | BRAF | CRKL | FBXW7 | IGF1R | MLH3 | PDGFRB | SF3B1 | WT1 |
| ACVR1B | BRCA1 | CRLF2 | FGFR1 | IL7R | MLL2 | PHF6 | SMAD2 | XPO1 |
| AKT1 | BRCA2 | CSF1R | FGFR2 | INSRR | MLL3 | PIK3CA | SMAD4 | |
| AKT2 | BRD4 | CTNNB1 | FGFR3 | IRS2 | MPL | PIK3CB | SMARCA4 | |
| AKT3 | BRIP1 | CYLD | FGFR4 | JAK1 | MRE11A | PIK3R1 | SMARCB1 | |
| ALK | C11orf30 | DAXX | FH | JAK2 | MSH2 | PMS1 | SMO | |
| APC | CARD11 | DDR2 | FLCN | JAK3 | MSH6 | PMS2 | SOCS1 | |
| AR | CASP8 | DNMT1 | FLT1 | KDM5C | MSR1 | PPP2R1A | SOX9 | |
| ARAF | CBL | DNMT3A | FLT3 | KDM6A | MTOR | PRDM1 | SPOP | |
| ARID1A | CCDC6 | EGFR | FLT4 | KDR | MUTYH | PTCH1 | SRC | |
| ARID1B | CCND1 | ELAC2 | FOXL2 | KIF1B | MYD88 | PTEN | SRSF2 | |
| ARID2 | CCND2 | EP300 | FUBP1 | KIT | NBN | PTPN11 | STAG2 | |
| ASXL1 | CCND3 | EPCAM | GAB2 | KLF4 | NCOR1 | QC21 | STAT3 | |
| ATM | CCNE1 | EPHA2 | GATA1 | KMT2A | NF1 | RAD50 | STK11 | |
| ATR | CDC73 | EPHA3 | GATA2 | KRAS | NF2 | RAD51C | SYK | |
| ATRX | CDH1 | EPHA5 | GATA3 | MAP2K1 | NFE2L2 | RAF1 | TERT | |
| AURKA | CDK4 | ERBB2 | GNA11 | MAP2K2 | NOTCH1 | RARA | TET2 | |
| AURKB | CDK6 | ERBB3 | GNAQ | MAP3K1 | NOTCH2 | RB1 | TMEM127 | |
| AXIN1 | CDK8 | ERBB4 | GNAS | MAPK1 | NOTCH3 | RET | TNFAIP3 | |
| AXIN2 | CDKN1A | ERCC3 | H3F3A | MAX | NPM1 | RNASEL | TOP1 | |
| AXL | CDKN1B | ERG | HGF | MCL1 | NRAS | RNF43 | TP53 | |
| B2M | CDKN2A | ESR1 | HIST1H3B | MDM2 | NTRK1 | ROS1 | TRAF7 | |
| BAP1 | CDKN2B | EWSR1 | HNF1A | MDM4 | NTRK3 | RUNX1 | TSC1 | |
| BARD1 | CEBPA | EXT1 | HRAS | MED12 | PALB2 | SDHAF2 | TSC2 | |
| BCL2 | CHEK1 | EXT2 | HSD17B3 | MEN1 | PAX5 | SDHB | TSHR | |
| BCOR | CHEK2 | EZH2 | HSD3B2 | MET | PBRM1 | SDHC | U2AF1 | |
| BCR | CIC | FAM123B | IDH1 | MITF | PCM1 | SETBP1 | VEGFA | |

2. Analysis of Sequencing Result

One patient with small pulmonary nodules was subjected to sequencing and analysis according to the method described in Example 1, wherein the chip ONCOcare-ZS of the present example was used in the step of enrichment and capture with probes. The statistical results of the sequencing data are shown in Table 4 below:

TABLE 4

| | | | sequencing results | | |
|---|---|---|---|---|---|
| Sample name | Size of nodules | Total data output(G) | Matching rate of the forward and reverse strands | Low-frequency error-correction depth | Effective data utilization ratio |
| CD148 | 0.7 cm × 0.5 cm × 0.3 cm | 13.2 | 76.62% | 1153.6X | 3.78% |

Note:
Matching rate of the forward and reverse strands: the ratio of the clusters present on both forward and reverse strands of 3 tested sequences to overall clusters on the 3 tested sequences, to evaluate the matching circumstance of forward and reverse strands in the available data; Effective data utilization ratio: the ratio of the number of tested sequences at least satisfying 2+/2− cluster after error correction to the total number of tested sequences; Low-frequency error-correction depth: average coverage for the bases in the target region after effective error correction of data.

Analysis of the results: Two driver mutations, TP53 p. [Val272Leu] and EGFR p. [Leu861Arg] were detected in the plasma of the patient, indicating that the patient had a higher risk of cancer. It was confirmed by subsequent clinical pathology that the patient had invasive adenocarcinoma T1aN0M0, IA. In addition, conventional high-throughput sequencing analysis of corresponding tissue and plasma and plasma digital PCR validation results were shown as follows:

TABLE 5

| Gene | cHGVS | pHGVS | Mutation frequency by Conventional tissue NGS analysis | Mutation frequency by Conventional plasma NGS analysis | Mutation frequency by Digital PCR | Mutation frequency by ER-seq |
|---|---|---|---|---|---|---|
| TP53 | c.[814G > T] | p.[Val272Leu] | 13% | — | 0.13% | 0.4% |
| EGFR | c.[2582T > G] | p.[Leu861Arg] | 3% | — | — | 0.15% |

Example 4 Instructing Individualized Medication Against Tumor

1. Chip Design

A probe, ONCOcare-drug, for instructing individualized medication against tumor was completed based on the design principle of enrichment probe chips. The chip includes high-frequency genes of 12 kinds of common cancers, important genes in 12 signaling pathways of cancer, common target drug and chemotherapeutic drug genes, totaling 559 genes, 850 KB, 2,400 hotspot target mutations. The gene list is shown in Table 6.

TABLE 6

Gene list of the chip ONCOcare-drug for instructing individualized medication against tumor

| | | | | | | | | |
|---|---|---|---|---|---|---|---|---|
| ABL1 | C1R | DIS3 | FGF19 | HSPA4 | MIR142 | PAX5 | RB1 | SRSF2 |
| ABL2 | C1S | DNMT1 | FGF23 | IDH1 | MITF | PBRM1 | REL | SSTR2 |
| ACVR1B | CARD11 | DNMT3A | FGF3 | IDH2 | MLH1 | PCBP1 | RET | STAG2 |
| ACVR2A | CASP8 | DOT1L | FGF4 | IFNAR1 | MLH3 | PCM1 | RHEB | STAT4 |
| AJUBA | CBFB | DUSP6 | FGF6 | IFNAR2 | MLL | PDGFRA | RICTOR | STAT5B |
| AKT1 | CBL | EDNRA | FGF7 | IGF1 | MLL2 | PDGFRB | RNASEL | STK11 |
| AKT2 | CBLB | EGFR | FGFR1 | IGF1R | MLL3 | PDK1 | RNF43 | SUFU |
| AKT3 | CBR1 | EGR3 | FGFR2 | IGF2 | MLL4 | PHF6 | ROBO1 | SUZ12 |
| ALK | CCND1 | EIF4A2 | FGFR3 | IKBKB | MPL | PIGF | ROBO2 | SYK |
| ALOX12B | CCND2 | ELAC2 | FGFR4 | IKBKE | MRE11A | PIK3C2A | ROS1 | TAF1 |
| ANGPT1 | CCND3 | ELF3 | FH | IKZF1 | MS4A1 | PIK3C2B | RPA1 | TBL1XR1 |
| ANGPT2 | CCNE1 | EML4 | FLCN | IL7R | MSH2 | PIK3C2G | RPL22 | TBX3 |
| APC | CD79A | EP300 | FLT1 | INHBA | MSH3 | PIK3C3 | RPL5 | TEK |
| APCDD1 | CD79B | EPCAM | FLT3 | IRF4 | MSH4 | PIK3CA | RPS14 | TERT |
| AR | CDC25C | EPHA2 | FLT4 | IRS2 | MSH5 | PIK3CB | RPS6KB1 | TET2 |
| ARAF | CDC42 | EPHA3 | FNTA | ITGB2 | MSH6 | PIK3CG | RPTOR | TFG |

TABLE 6-continued

Gene list of the chip ONCOcare-drug for instructing individualized medication against tumor

| | | | | | | | | | |
|---|---|---|---|---|---|---|---|---|---|
| ARFRP1 | CDC73 | EPHA5 | FOXA1 | JAK1 | MSR1 | PIK3R1 | RUNX1 | TGFBR2 | |
| ARHGAP35 | CDH1 | EPHB1 | FOXA2 | JAK2 | MTOR | PIK3R2 | RUNX1T1 | TIPARP | |
| ARID1A | CDK12 | EPHB2 | FOXL2 | JAK3 | MUC1 | PLK1 | RXRA | TLR4 | |
| ARID1B | CDK2 | EPHB6 | FPGS | JUN | MUTYH | PML | RXRB | TMEM127 | |
| ARID2 | CDK4 | EPPK1 | FUBP1 | KAT6A | MYC | PMS1 | RXRG | TNFAIP3 | |
| ARID5B | CDK6 | ERBB2 | FYN | KDM5A | MYCL1 | PMS2 | SDHAF2 | TNFRSF14 | |
| ASXL1 | CDK8 | ERBB3 | GAB2 | KDM5C | MYCN | PNRC1 | SDHB | TNFRSF8 | |
| ATM | CDKN1A | ERBB4 | GATA1 | KDM6A | MYD88 | POLQ | SDHC | TNFSF11 | |
| ATR | CDKN1B | ERCC2 | GATA2 | KDR | NAV3 | PPP2R1A | SDHD | TNFSF13B | |
| ATRX | CDKN2A | ERCC3 | GATA3 | KEAP1 | NBN | PRDM1 | SEMA3A | TOP1 | |
| AURKA | CDKN2B | ERG | GID4 | KIF1B | NCOA1 | PRKAA1 | SEMA3E | TOP2A | |
| AURKB | CDKN2C | ESR1 | GNA11 | KIF5B | NCOA2 | PRKAR1A | SETBP1 | TOP2B | |
| AXIN1 | CDX2 | ETV1 | GNA13 | KIT | NCOR1 | PRKCA | SETD2 | TP53 | |
| AXIN2 | CEBPA | ETV6 | GNAQ | KLF4 | NEK11 | PRKCB | SF1 | TRAF7 | |
| AXL | CFLAR | EWSR1 | GNAS | KLHL6 | NF1 | PRKCG | SF3B1 | TSC1 | |
| B2M | CHD1 | EXT1 | GNRHR | KRAS | NF2 | PRKDC | SH2B3 | TSC2 | |
| B4GALT3 | CHD2 | EXT2 | GPR124 | LCK | NFE2L2 | PRSS8 | SIN3A | TSHR | |
| BACH1 | CHD4 | EZH2 | GRIN2A | LIMK1 | NFE2L3 | PSMB1 | SLAMF7 | TSHZ2 | |
| BAK1 | CHEK1 | FAM123B | GRM3 | LRRK2 | NFKBIA | PSMB2 | SLC4A1 | TSHZ3 | |
| BAP1 | CHEK2 | FAM46C | GSK3B | LYN | NKX2-1 | PSMB5 | SLIT2 | TUBA1A | |
| BARD1 | CHUK | FANCA | H3F3A | MALAT1 | NKX3-1 | PTCH1 | SMAD2 | TUBB | |
| BCL2 | CIC | FANCC | H3F3C | MAP2K1 | NOTCH1 | PTCH2 | SMAD3 | TUBD1 | |
| BCL2A1 | CRBN | FANCD2 | HCK | MAP2K2 | NOTCH2 | PTEN | SMAD4 | TUBE1 | |
| BCL2L1 | CREBBP | FANCE | HDAC1 | MAP2K4 | NOTCH3 | PTP4A3 | SMARCA1 | TUBG1 | |
| BCL2L11 | CRIPAK | FANCF | HDAC2 | MAP3K1 | NOTCH4 | PTPN11 | SMARCA4 | TYR | |
| BCL2L2 | CRKL | FANCG | HDAC3 | MAP3K13 | NPM1 | PTPRD | SMARCB1 | U2AF1 | |
| BCL6 | CRLF2 | FANCI | HDAC4 | MAPK1 | NR3C1 | RAC1 | SMARCD1 | USP9X | |
| BCOR | CROT | FANCL | HDAC6 | MAPK3 | NRAS | RAC2 | SMC1A | VEGFA | |
| BCORL1 | CSF1R | FANCM | HDAC8 | MAPK8 | NSD1 | RAD21 | SMC3 | VEGFB | |
| BCR | CTCF | FAT3 | HGF | MAPK8IP1 | NTRK1 | RAD50 | SMO | VEZF1 | |
| BLM | CTLA4 | FBXW7 | HIF1A | MAX | NTRK2 | RAD51 | SOCS1 | VHL | |
| BMPR1A | CTNNA1 | FCGR1A | HIST1H1C | MC1R | NTRK3 | RAD51B | SOX10 | WHSC1L1 | |
| BRAF | CTNNB1 | FCGR2A | HIST1H2BD | MCL1 | NUP93 | RAD51C | SOX17 | WISP3 | |
| BRCA1 | CUL4A | FCGR2B | HIST1H3B | MDM2 | PAK3 | RAD51D | SOX2 | WWP1 | |
| BRCA2 | CUL4B | FCGR2C | HNF1A | MDM4 | PAK7 | RAD52 | SOX9 | XIAP | |
| BRIP1 | CYLD | FCGR3A | HRAS | MECOM | PALB2 | RAD54L | SPEN | XPA | |
| BTG1 | CYP17A1 | FCGR3B | HRH2 | MED12 | PARP1 | RAF1 | SPOP | XPC | |
| BTK | DAXX | FGF10 | HSD17B3 | MEF2B | PARP2 | RARA | SPRY4 | XPO1 | |
| C11orf30 | DDR1 | FGF12 | HSD3B2 | MEN1 | PARP3 | RARB | SRC | XRCC3 | |
| C1QA | DDR2 | FGF14 | HSP90AA1 | MET | PARP4 | RARG | SRD5A2 | YES1 | |
| ZNF217 | ZNF703 | ZRSR2 | WT1 | XRCC1 | GSTP1 | ERCC1 | MTHFR | SOD2 | |
| UMPS | UGT1A1 | CBR3 | ATIC | MTRR | DPYD | TPMT | | | |

2. Analysis of Sequencing Result

One patient with advanced colorectal disease was analyzed according to the method described in Example 1, wherein the chip ONCOcare-Drug of the present example was used in the step of enrichment and capture with probes. The statistical results of the sequencing data are shown in Table 7 below:

TABLE 7

| Sample name | Clinical stages | Total data output(G) | Matching rate of the forward and reverse strands | Low-frequency error-correction depth | Effective data utilization ratio |
|---|---|---|---|---|---|
| CD160 | IV stage metastasis | 5.5 | 78.2% | 520X | 4.1% |

Note:
Matching rate of the forward and reverse strands: the ratio of the clusters present on both forward and reverse strands of 3 tested sequences to overall clusters on the 3 tested sequences, to evaluate matching circumstance of forward and reverse strands in the available data; Effective data utilization ratio: the ratio of the number of tested sequences at least satisfying 2+/2− cluster after error correction to the total number of tested sequences; Low-frequency error-correction depth: average coverage for the bases in the target region after effective error correction of data.

Analysis of the results: A total of 6 non-synonymous mutations in the Exon region were detected, and they were consistent with tissue mutations. Details of the mutations are shown in Table 8:

TABLE 8

| Gene | Mutation of bases | Mutation of amino acids | Mutation type | Mutation frequency by ER-seq | Tissue mutation frequency |
|---|---|---|---|---|---|
| TP53 | c.C241T | p.R81X | mutation resulting in a termination codon | 10.4% | 32.8% |
| APC | c.1254T > A | p.N418K | missense mutation | 6.3% | 25.6% |
| KRAS | c.35G > A | p.G12D | missense mutation | 3.8% | 20.3% |
| ALMS1 | c.T3971G | p.V1324G | missense mutation | 1.2% | 15.4% |
| MLH1 | c.A1427T | p.E476V | missense mutation | 2.5% | 13.8% |
| ZNF721 | c.C2061G | p.H687Q | missense mutation | 0.83% | 10.2% |

The details for chemotherapy sites are shown in

TABLE 9

| Gene name | RS number | Detected base | Gene name | RS number | Detected base |
|---|---|---|---|---|---|
| XPC | rs2228001 | GT | MTHFR | rs1801133 | AA |
| TP53 | rs1042522 | CC | CBR3 | rs1056892 | GG |
| XRCC1 | rs25487 | CC | MTHFR | rs1801133 | AA |
| GSTP1 | rs1695 | AG | ATIC | rs4673993 | TT |
| ERCC1 | rs11615 | GG | MTRR | rs1801394 | AA |
| ERCC1 | rs3212986 | CC | TP53 | rs1042522 | CC |
| MTHFR | rs1801133 | AA | DPYD | rs3918290 | CC |
| SOD2 | rs4880 | AA | DPYD | rs67376798 | TT |
| GSTP1 | rs1695 | AG | TPMT | rs1800460 | CC |
| MTHFR | rs1801133 | AA | TPMT | rs1800462 | CC |
| MTHFR | rs1801131 | TT | TPMT | rs1800584 | CC |
| GSTP1 | rs1695 | AG | UGT1A1 | rs8175347 | 7TA/7TA |
| UMPS | rs1801019 | GG | | | |

Drug prediction: the database was interpreted in combination with the above detection results based on the target drug chemotherapy. The following conclusions were only for clinician's reference during development of therapeutic schedule:

TABLE 10

| | Medication prompts for targeted drugs | | | | | |
|---|---|---|---|---|---|---|
| | Being recommended for colorectal cancer by FDA | | Being recommended for other cancers by FDA | | Clinical II/III stage medicine | |
| Gene mutation | Positive correlation | Negative correlation | Positive correlation | Negative correlation | Positive correlation | Negative correlation |
| KRAS p.G12D | No | Everolimus | No | No | Selumetinib Antroquinonol | No |

TABLE 11

| | Medication prompts for chemotherapeutics | |
|---|---|---|
| Efficacy prediction | Drugs recommended by FDA (colorectal cancer) | Drugs recommended by FDA (other cancers) |
| Low risk of toxic and side effects or high drug sensitivity | Capecitabine, fluorouracil | paclitaxel/docetaxel, purine compounds/ purine analogues |
| High risk of toxic and side effects or low drug sensitivity | No | anthracycline, cyclophosphamide |

Example 5 Postoperative Monitoring of 12 Kinds of Common Cancers

1. Chip Design

A chip, ONCOcare-JK, for postoperative monitoring of tumors (lung cancer, colorectal cancer, gastric cancer, breast cancer, kidney cancer, pancreatic cancer, ovarian cancer, endometrial cancer, thyroid cancer, cervical cancer, esophageal cancer and liver cancer, etc.) was completed based on the design principle of enrichment probe chips. The chip includes Driver Genes related with common cancers with high incidence, high-frequency mutant genes, important genes in 12 cancer-related signaling pathways, totaling 508 genes, 500 Kb, 4,800 hotspot mutations. The gene list is shown in table 12.

TABLE 12

| Gene list for the postoperative monitoring chip ONCOcare-JK | | | | | | | | |
|---|---|---|---|---|---|---|---|---|
| ABL1 | CBLB | DOT1L | FGF7 | IGF2 | MSH2 | PIK3CB | SDHB | TRAF7 |
| ABL2 | CBR1 | DUSP6 | FGFR1 | IKBKB | MSH3 | PIK3CG | SDHC | TSC1 |
| ACVR1B | CCND1 | EDNRA | FGFR2 | IKBKE | MSH4 | PIK3R1 | SDHD | TSC2 |
| ACVR2A | CCND2 | EGFR | FGFR3 | IKZF1 | MSH5 | PIK3R2 | SEMA3A | TSHR |
| AJUBA | CCND3 | EGR3 | FGFR4 | IL7R | MSH6 | PLK1 | SEMA3E | TSHZ2 |
| AKT1 | CCNE1 | EIF4A2 | FLCN | INHBA | MSR1 | PML | SETBP1 | TSHZ3 |
| AKT2 | CD79A | ELAC2 | FLT1 | IRF4 | MTOR | PMS1 | SETD2 | TUBA1A |
| AKT3 | CD79B | ELF3 | FLT3 | IRS2 | MUC1 | PMS2 | SF1 | TUBB |
| ALK | CDC25C | EML4 | FLT4 | ITGB2 | MUTYH | PNRC1 | SF3B1 | TUBD1 |
| ANGPT1 | CDC42 | EP300 | FNTA | JAK1 | MYC | POLQ | SH2B3 | TUBE1 |
| ANGPT2 | CDC73 | EPHA2 | FOXA1 | JAK2 | MYCL1 | PPP2R1A | SIN3A | TUBG1 |
| APC | CDH1 | EPHA3 | FOXA2 | JAK3 | MYCN | PRDM1 | SLAMF7 | TYR |
| AR | CDK12 | EPHA5 | FOXL2 | JUN | NAV3 | PRKCA | SLC4A1 | VEGFA |
| ARAF | CDK2 | EPHB1 | FPGS | KDR | NBN | PRKCB | SLIT2 | VEGFB |
| ARFRP1 | CDK4 | EPHB2 | FUBP1 | KEAP1 | NCOA1 | PRKCG | SMAD2 | VEZF1 |
| ARID1A | CDK6 | EPHB6 | FYN | KIF1B | NCOA2 | PRKDC | SMAD3 | VHL |
| ARID1B | CDK8 | EPPK1 | GAB2 | KIF5B | NCOR1 | PRSS8 | SMAD4 | WISP3 |
| ASXL1 | CDKN1A | ERBB2 | GATA1 | KIT | NEK11 | PSMB1 | SMARCA1 | WT1 |
| ATM | CDKN1B | ERBB3 | GATA2 | KLF4 | NF1 | PSMB2 | SMC1A | WWP1 |
| ATR | CDKN2A | ERBB4 | GATA3 | KLHL6 | NF2 | PSMB5 | SMC3 | XIAP |
| ATRX | CDKN2B | ERCC2 | GID4 | KRAS | NOTCH1 | PTCH1 | SMO | XPA |
| AURKA | CDKN2C | ERCC3 | GNA11 | LCK | NOTCH2 | PTCH2 | SOCS1 | XPC |
| AURKB | CDX2 | ERG | GNA13 | LIMK1 | NOTCH3 | PTEN | SOX2 | XPO1 |
| AXIN1 | CEBPA | ESR1 | GNAQ | LRRK2 | NOTCH4 | PTP4A3 | SOX9 | XRCC3 |
| AXIN2 | CFLAR | ETV1 | GNAS | MALAT1 | NPM1 | PTPN11 | SPEN | YES1 |
| AXL | CHD1 | ETV6 | GNRHR | MAP2K1 | NR3C1 | PTPRD | SPRY4 | ZNF217 |
| BACH1 | CHD2 | EWSR1 | GPR124 | MAP2K2 | NRAS | RAC1 | SRC | ZRSR2 |
| BAK1 | CHD4 | EXT1 | GRIN2A | MAP2K4 | NSD1 | RAC2 | SRD5A2 | |
| BAP1 | CHEK1 | EXT2 | GRM3 | MAP3K1 | NTRK1 | RAD21 | SRSF2 | |
| BARD1 | CHEK2 | EZH2 | GSK3B | MAP3K13 | NTRK2 | RAD50 | SSTR2 | |
| BCL2 | CHUK | FAM46C | H3F3A | MAPK1 | NTRK3 | RAD51 | STAG2 | |
| BCL2A1 | CIC | FANCA | H3F3C | MAPK3 | NUP93 | RAF1 | STAT4 | |
| BCL2L1 | CRBN | FANCC | HCK | MAPK8 | PAK3 | RARA | STAT5B | |
| BCL2L2 | CREBBP | FANCD2 | HDAC1 | MAX | PAK7 | RARB | STK11 | |
| BCL6 | CRIPAK | FANCE | HDAC2 | MC1R | PALB2 | RARG | SUFU | |
| BCOR | CRKL | FANCF | HDAC3 | MCL1 | PARP1 | RB1 | SUZ12 | |
| BCORL1 | CRLF2 | FANCG | HDAC4 | MDM2 | PARP2 | REL | SYK | |
| BCR | CTCF | FANCI | HDAC6 | MDM4 | PARP3 | RET | TAF1 | |
| BLM | CTLA4 | FANCL | HDAC8 | MED12 | PARP4 | RHEB | TBX3 | |
| BMPR1A | CTNNA1 | FANCM | HGF | MEF2B | PCM1 | RNF43 | TEK | |
| BRAF | CTNNB1 | FAT3 | HIF1A | MEN1 | PDGFRA | ROBO1 | TERT | |
| BRCA1 | CUL4A | FBXW7 | HNF1A | MET | PDGFRB | ROBO2 | TET2 | |
| BRCA2 | CUL4B | FCGR2A | HRAS | MITF | PDK1 | ROS1 | TFG | |
| BRIP1 | CYLD | FCGR2B | HRH2 | MLH1 | PHF6 | RPA1 | TGFBR2 | |
| BTG1 | DAXX | FCGR2C | IDH1 | MLH3 | PIGF | RPL5 | TIPARP | |
| BTK | DDR1 | FCGR3A | IDH2 | MLL | PIK3C2A | RPS14 | TLR4 | |
| CARD11 | DDR2 | FCGR3B | IFNAR1 | MLL2 | PIK3C2B | RXRA | TOP1 | |
| CASP8 | DIS3 | FGF3 | IFNAR2 | MLL3 | PIK3C2G | RXRB | TOP2A | |
| CBFB | DNMT1 | FGF4 | IGF1 | MLL4 | PIK3C3 | RXRG | TOP2B | |
| CBL | DNMT3A | FGF6 | IGF1R | MS4A1 | PIK3CA | SDHAF2 | TP53 | |

2. Analysis of Sequencing Result

One patient with lung adenocarcinoma who had an operation 3 months ago, was analyzed according to the method described in Example 1, wherein the chip ONCOcare-JK of the present example was used in the step of enrichment and capture with probes. The statistical results of the sequencing data are shown in Table 13 below:

TABLE 13

| Sample name | Clinical information | Total data output(G) | Matching rate of the forward and reverse strands | Low-frequency error-correction depth | Effective data utilization ratio |
| --- | --- | --- | --- | --- | --- |
| CD172 | Right middle lung adenocarcinoma T2aN0M0 Ib stage, 3 months after operation | 10 | 73.4% | 920X | 3.92% |

Note:
Matching rate of the forward and reverse strands: the ratio of the clusters present on both forward and reverse strands of 3 tested sequences to overall clusters on the 3 tested sequences, to evaluate matching circumstance of forward and reverse strands in the available data; Effective data utilization ratio: the ratio of the number of tested sequences at least satisfying 2+/2− cluster after error correction to the total number of tested sequences; Low-frequency error-correction depth: average coverage for the bases in the target region after effective error correction of data.

Analysis of the results: A total of 5 non-synonymous mutations in the Exon region were detected, and details of the mutations are shown in Table 14:

TABLE 14

| Mutation results of original carcinoma tissue sample | | | | | Plasma monitoring results at 3 month after operation | | | | |
| --- | --- | --- | --- | --- | --- | --- | --- | --- | --- |
| Gene | Mutation of bases | Mutation of amino acids | Mutation type | Mutation frequency | Gene | Mutation of bases | Mutation of amino acids | Mutation type | Mutation frequency |
| TP53 | c.814G > T | p.V272L | missense mutation | 18% | NOTCH1 | c.2054A > C | p.N685T | missense mutation | 1.63% |
| PDGFRA | c.2235G > A | p.M745I | missense mutation | 11.5% | PDGFRA | c.2235G > A | p.M745I | missense mutation | 1.02% |
| ROS1 | c.6316G > A | p.A2106T | missense mutation | 10% | AR | c.1369_1371 delGGC | p.G457del | missense mutation | 0.89% |
| PTCH1 | c.49_51del GGC | p.G17del | Deletion mutation | 8% | MEF2B | c.844A > G | p.R282G | missense mutation | 0.76% |
| SETD2 | c.22C > T | p.P8S | missense mutation | 7.6% | PML | c.851G > C | p.R284P | missense mutation | 0.47% |
| NOTCH1 | c.2054A > C | p.N685T | missense mutation | 6.2% | | | | | |
| FUBP1 | c.121A > T | p.I41F | missense mutation | 5.3% | | | | | |

A total of 19 mutations were detected, wherein 5 mutations were non-synonymous mutations in Exon. Relative to normal human baseline, the detected mutations were higher. In addition, NOTCH1 p.N685T and PDGFRA p.M745I present in the tissues still existed in the plasma after operation, indicating that there may be a higher risk of recurrence after operation. Clinical follow-up: there was a progress in disease of the patient. In addition, conventional high-throughput sequencing analysis of plasma and plasma digital PCR validation results were shown in table 15:

TABLE 15

| Gene | cHGVS | pHGVS | Mutation frequency by Conventional plasma NGS analysis | Mutation frequency by Digital PCR | Mutation frequency by ER-seq |
| --- | --- | --- | --- | --- | --- |
| NOTCH1 | c.2054A > C | p.N685T | 0.78% | 1.1% | 1.63% |
| PDGFRA | c.2235G > A | p.M745I | — | 0.42% | 1.02% |

Industrial Practical Applicability

The method for enrichment and sequencing of low-frequency mutations of target DNA in plasma, provided in the present invention, can accurately detect low-frequency of plasma DNA in 5-10 mL peripheral blood samples, with simple operation and strong practical applicability. In addition, the method has the following effects: high sensitivity, such that mutations at a low-frequency of 0.01% can be detected with high specificity; high specificity such that accurate detection of low-frequency mutations can be more effectively achieved with a specificity of 98% or greater; high-throughput, such that not only relevant genes of interest can be scanned at once to obtain more comprehensive information of the subject and more accurate relevant prediction, but also multiple samples can be detected simultaneously in a very short period of time, thereby reducing costs and facilitating clinical promotion; multidimensional applicability, such that this method can fully exploit the potential of plasma ctDNA, and lays a solid foundation for early screening, postoperative monitoring and accurate medical treatment of a variety of related tumors, thereby giving a big push to the development of clinical oncology.

What is claimed is:

1. A method for identifying low-frequency mutations in a target DNA present in plasma obtained from human peripheral blood, comprising the following steps:
    (1) extracting the target DNA from the plasma and constructing a DNA library containing fragments from the extracted target DNA;
    (2) amplifying and enriching such DNA fragments in the library containing predetermined mutations by first determining the Tm value of the library followed by universal library TT-COLD PCR;
    (3) enriching for fragments containing low-frequency mutations using hybridization capture probes and then amplifying and sequencing the resulting hybridization capture products which include fragments containing low-frequency mutations; and
    (4) analyzing the sequences of the fragments containing the low-frequency mutations using a forward and reverse double-strand error correction procedure so as to identify low-frequency mutations in the target DNA.

2. The method according to claim 1, wherein the DNA library in step (1) is constructed according to a three-step enzymatic reaction comprising terminal repair, addition of "A", and library linker ligation.

3. The method according to claim 1, wherein step (2) comprises
    bypassing the specific Tc values for each DNA fragment in the library, enriching all the DNA fragments in the library using a pair of universal primers under one serial cycling condition, setting Tc min≈TM-2.5, followed by a gradual increase in Tc at a rate of 0.5° C., and performing full cold PCR under each Tc condition, respectively.

4. The method according to claim 1, wherein the Tm value of the library in step (2) is determined by a method comprising the following:
    a) amplifying by fluorescence quantitative PCR free target DNA from normal human plasma in a ligation library using a pair of primers to obtain a melting curve, and
    b) obtaining the Tm value of the library from analysis of the melting curve;
    wherein the nucleotide sequence of the pair of primers is the following:

```
upstream primer:
                                            (SEQ ID NO: 3)
AATGATACGGCGACCACCGAGATCTACACTCTTTCCCTACACGACGCTCT TCCGATCT,
and downstream primer:
                                            (SEQ ID NO: 4)
CAAGCAGAAGACGGCATACGAGATxxxxxxxxGTGACTGGAGTTCAGACG

TGTGCTCTTCCGATCT,
``` where xxxxxxxx is an index tag.

5. The method according to claim 3, wherein the pair of universal primers in step (2) is a pair of universal library TT-COLD PCR primers, the nucleotide sequence of which is the following:

```
upstream primer:
                                            (SEQ ID NO: 3)
AATGATACGGCGACCACCGAGATCTACACTCTTTCCCTACACGACGCTCT TCCGATCT,
and downstream primer:
                                            (SEQ ID NO: 4)
CAAGCAGAAGACGGCATACGAGATxxxxxxxxGTGACTGGAGTTCAGACG

TGTGCTCTTCCGATCT,
``` where xxxxxxxx is an index tag.

6. The method according to claim 3, wherein the one serial cycling condition is in the following:

| | | |
|---|---|---|
| 98° C. | 30 sec | — |
| 98° C. | 10 sec | 3 cycles |
| 55-65° C. | 15 sec | |
| 72° C. | 30 sec | |
| 98° C. | 10 sec | 4 cycles |
| 70° C. | 2 min | |
| Tc1 = TM-2° C. | 20 sec | |
| 55-65° C. | 15 sec | |
| 72° C. | 30 sec | |
| ... | Tc2; Tc3; Tc4 (ΔT = 0.5° C.) | 4 cycles/Tc |
| 98° C. | 10 sec | 4 cycles |
| 70° C. | 2 min | |
| Tc5 = TM-0° C. | 20 sec | |
| 55-65° C. | 15 sec | |
| 72° C. | 30 sec | |
| 72° C. | 2 min | — |
| 4° C. | Storage | —. |

7. The method according to claim 1, wherein the enriching in step (3) comprises using an enrichment probe chip for hybridization capture after the amplified library is qualified in quality control and the hybridization capture products are amplified and sequenced;
    wherein the enrichment probe chip is designed according to the following: the capture range of the chip is determined based on the purpose of the target gene, at least one hotspot mutation site is determined within a certain base range with reference to the database to which the target DNA belongs, with several primary types of mutations among multiple mutation types present with respect to this site taken for reference, and the corresponding frequency of occurrence is used as the proportion occupied by the mutation type in the total probe coverage level at the site,
    wherein a probe designed based on the human genome reference sequence hg19 is replaced with a probe designed based on a mutant base of the hotspot mutation, with the probes for other sites remaining unchanged, and the difference ratio between the total coverage of the probe for the hotspot mutation and the coverage of normal probe for the other sites is not less than 3:1, so as to achieve enrichment of the hotspot mutation during capture.

8. The method according to claim 1, wherein the forward and reverse double-strand error correction procedure in step (4) is the following:
    1) based on the sequencing results, the first 12 bp bases of a tested sequence 1 and the first 12 bp bases of a tested sequence 2 of paired tested sequences are cut as tags, arranged according to alphabetical order, and connected having to form an index of 24 bp, while forward and reverse strands are selected according to the arrangement and combination of the tags of the tested sequences;

2) external sorting is carried out on the index to achieve the purpose of gathering together all the tested sequences of the same DNA template;
3) center clustering is carried out on the gathered tested sequences having the same index, each large cluster with the same index is gathered into small clusters according to the Hamming distance between the sequences, with the Hamming distance between any two pairs of paired tested sequences in each small cluster not exceeding 10, so as to achieve the purpose of distinguishing tested sequences having the same index but coming from different DNA templates;
4) repeated clusters of the same DNA template obtained in step 3) are screened, and if the numbers of tested sequences of the forward strand and the reverse strand both reach two pairs or more, subsequent analysis is performed;
5) the clusters that satisfy the conditions in 4) are corrected to generate a pair of error-free new tested sequences, and for each sequenced base in the DNA template, if a certain base type of the sequenced base in the tested sequence of the forward strand reaches a consistence rate of 80% and in the tested sequence of the reverse strand also reaches a consistence rate of 80%, the base type for this base in the new tested sequence is recorded as this base type, thereby obtaining a new tested sequence which represents the original DNA template sequence;
6) the new tested sequence is aligned again with the genome by bwa mem algorithm, and a tested sequence with an alignment quality of less than 30 is screened out;
7) statistics is carried out based on the tested sequences obtained in step 6) to obtain the base type distribution for each site, the coverage of the statistical target region, the average sequencing depth, the forward and reverse strand matching ratio, and the low-frequency mutation rate in the capture region;
8) SNV/InDel/SV/CNV is called based on the alignment of information between the sample from a patient and a control, mutect process is used to call somatic SNV mutation, gatk process is used to call somatic InDel mutation, contra.py process is used to call CNV, and somVar process is used to call SV, wherein the screening parameters used are the following: control site mutation rate ≤2%, the number of varied tested sequences after error correction ≥2, and mutation prediction p value ≤0.05; and
9) the varied function, the support number of the varied tested sequence, the frequency of mutation, amino acid mutation, and the condition of such mutation in an existing mutation database are annotated.

9. The method according to claim 8, wherein in step 1), based on the sequence bases at the two ends of an inserted fragment, each fragment will form a pair of paired tested sequences by paired-end sequencing; the first 12 bp bases of a tested sequence 1 and the first 12 bp bases of a tested sequence 2 of paired tested sequences are taken as tags, arranged according to alphabetical order, and connected to form an index of 24 bp; and using the 24 bp as an index of the paired tested sequences, a strand is marked as a forward strand if the tag of the tested sequence 1 is in the front and a strand is marked as a reverse strand if the tag of the tested sequence 2 is in the front.

* * * * *

```
                           SEQUENCE LISTING

<160> NUMBER OF SEQ ID NOS: 4

<210> SEQ ID NO 1
<211> LENGTH: 34
<212> TYPE: DNA
<213> ORGANISM: Artificial sequence
<220> FEATURE:
<223> OTHER INFORMATION: Laboratory synthesis

<400> SEQUENCE: 1
tacactcttt ccctacacga cgctcttccg atct                              34

<210> SEQ ID NO 2
<211> LENGTH: 33
<212> TYPE: DNA
<213> ORGANISM: Artificial sequence
<220> FEATURE:
<223> OTHER INFORMATION: Laboratory synthesis

<400> SEQUENCE: 2
gatcggaaga gcacacgtct gaactccagt cac                               33

<210> SEQ ID NO 3
<211> LENGTH: 58
<212> TYPE: DNA
<213> ORGANISM: Artificial sequence
<220> FEATURE:
<223> OTHER INFORMATION: Laboratory synthesis

<400> SEQUENCE: 3
aatgatacgg cgaccaccga gatctacact ctttccctac acgacgctct tccgatct    58

<210> SEQ ID NO 4
<211> LENGTH: 66
<212> TYPE: DNA
<213> ORGANISM: Artificial sequence
<220> FEATURE:
<223> OTHER INFORMATION: Laboratory synthesis
<220> FEATURE:
<221> NAME/KEY: misc_feature
<222> LOCATION: (25)..(32)
<223> OTHER INFORMATION: n is a, c, g, or t

<400> SEQUENCE: 4
caagcagaag acggcatacg agatnnnnnn nngtgactgg agttcagacg tgtgctcttc  60
cgatct                                                            66
```